(12) United States Patent
Streeper et al.

(10) Patent No.: US 7,888,051 B2
(45) Date of Patent: Feb. 15, 2011

(54) METHOD OF IDENTIFYING BIOMARKERS IN HUMAN SERUM INDICATIVE OF PATHOLOGIES OF HUMAN LUNG TISSUES

(75) Inventors: Robert T. Streeper, San Antonio, TX (US); Elzbieta Izbicka, San Antonio, TX (US); Sung H. Baek, Snohomish, WA (US)

(73) Assignee: Cancer Prevention and Cure, Ltd., Michigan City, IN (US)

( * ) Notice: Subject to any disclaimer, the term of this patent is extended or adjusted under 35 U.S.C. 154(b) by 330 days.

(21) Appl. No.: 12/208,437

(22) Filed: Sep. 11, 2008

(65) Prior Publication Data

US 2009/0068685 A1 Mar. 12, 2009

Related U.S. Application Data

(60) Provisional application No. 60/971,440, filed on Sep. 11, 2007.

(51) Int. Cl.
*G01N 33/53* (2006.01)
*G01N 31/00* (2006.01)

(52) U.S. Cl. .......................... 435/7.21; 435/7.1; 436/1; 436/501; 436/518; 424/9.1; 424/520; 422/1; 422/50; 422/61; 530/300; 530/350

(58) Field of Classification Search ........................ None
See application file for complete search history.

(56) References Cited

U.S. PATENT DOCUMENTS

2003/0190602 A1 10/2003 Pressman et al.

OTHER PUBLICATIONS

Bosse, et al., "Serum Matrix Metalloproteinase-9: Tissueinhibitor of Metalloproteinase-1 Ratio Correlates with Steroid Responsiveness in Moderate to Severe Athasma", American Journal of Respiratory and Critical Care Medicine, vol. 159, pp. 596-602.

Camilla, et al., "Flow Cytometric Microsphere-Based Immunoassay: Anaylisis of Secreted Cytokines in Whole-Blood Samples from Asthmatics", Luminex Publications—Journal: Clinical and Diagnostic Laboratory Immunology, pp. 776-784.

Koizumi, et al., "Elevation of Serum Soluble Vascular Cell Adhesion Molecule-1 (sVCAM-1) Levels in Bronchial Asthma", Clinical and Experimental Immunology, vol. 101, pp. 468-473, (Apr. 1995).

Huang, et al., "Human Non-Small Cell Lung Cancer Cells Express a Type 2 Cytokine Pattern", Cancer Research, vol. 55, pp. 3847-3853, (Sep. 2005).

Iizasa, "Elevated Levels of Circulating Plasma Matrix Metalloproteinase 9 in Non-Small Cell Lung Cancer Patients", Clinical Cancer Research, vol. 5, No. 1, pp. 149-153, (Jan. 1999).

Liu, et al., "Multiplexed Analysis of Biomarkers Related to Obesity and the Metabolic Syndrome in Human Plasma, Using the Luminex-100 System", Clinical Chemistry, vol. 51, No. 7, pp. 1102-1109 (Jul. 2005).

Leonardi, et al., "Matrix Metalloproteases in Vernal Keratoconjunctivitis, Nasal Polyps and Allergic Asthma", Clinical and Experimental Allergy, vol. 37, No. 6, pp. 872-879 (Jun. 2007).

International Search Report and the Written Opinion of the International Searching Authority, for International Application PCT/US08/75953, dated Nov. 19, 2008.

*Primary Examiner*—Lisa V Cook
(74) *Attorney, Agent, or Firm*—Hunton & Williams LLP

(57) ABSTRACT

A method of identifying altered biomarker expression levels in a human serum specimen to diagnose asthma or non-small celled lung cancers in humans. The existence of asthma or non-small celled lung cancers in a patient can be determined by subjecting a blood sample from the patient to a simple blood test to determine the expression levels of certain specific biomarkers. The expression levels of the specific biomarkers are compared to ranges of expression levels for the same biomarkers which are indicative of individuals known to have asthma, non-small cell lung cancers, or neither. Comparing the expression levels will determine the existence or non-existence of asthma or non-small cell lung cancer.

34 Claims, 20 Drawing Sheets

ASTHMA

| EGF (11) Fl - Bkgd | IL-5 (10) Fl - Bkgd | IL-4 (9) Fl - Bkgd | IL-1alpha (32) Fl - Bkgd | IL-7 (13) Fl - Bkgd | IL-6 (12) Fl - Bkgd | GM-CSF (39) Fl - Bkgd | IL-17 (30) Fl - Bkgd | IL-15 (28) Fl - Bkgd | TNF-alpha (40) Fl - Bkgd |
|---|---|---|---|---|---|---|---|---|---|
| 3267.9 | 642.5 | -41.3 | 1437.6 | -1491.9 | 2791.3 | 98.4 | 1560.5 | 12.3 | 931.8 |
| 3202.9 | -168.5 | -343.1 | -2462.4 | -1368.4 | 1349.8 | 863.9 | 738 | 104.3 | 628 |
| 4495.7 | 3637 | 2187.7 | 16386.1 | 406.1 | 3680.3 | 2408.4 | 1132.5 | 580.3 | 224.5 |
| 2878.7 | 3780.3 | 7763.4 | 20528.6 | -1262.7 | 15239.8 | 629.7 | 3562 | 184.8 | 2074.8 |
| 32.4 | -121 | -107.3 | 497.8 | -1520.4 | -334.7 | -188.6 | -23.5 | -38.2 | 114.5 |
| -29.8 | 12383.8 | 13482.7 | -1465.4 | 6725.3 | 17138.6 | -77.1 | 9354.8 | 48.8 | 402.8 |
| 1849.9 | 194.5 | 13.2 | -976.4 | -622.7 | 4966.6 | 380.9 | 4141.8 | 433.3 | 4118 |
| 1580.9 | 2113.8 | 1930.4 | 17871.8 | -1048.9 | 3421.8 | 695.2 | -42.3 | -6.9 | 433.3 |
| -52.6 | -144.3 | 174.9 | -2362.9 | -1165.2 | -806.7 | 13.4 | 1.8 | -24.7 | 416 |
| 5855.4 | -67 | -306.6 | -1749.7 | -358.2 | 1304.8 | 847.2 | 573.5 | 949.8 | 853.3 |
| 175.2 | -125 | -454.1 | -2604.4 | -298.9 | -835.7 | 197.4 | -20.5 | 25.8 | 570 |
| 8060.2 | 6806 | 12550.9 | 25079.6 | -1492.2 | 18071.8 | 871.4 | 250.5 | 13.8 | 474.3 |
| 6134.2 | 5325 | 11084.7 | 22068.6 | -1185.4 | 19947.6 | 315.4 | 5507 | 436.8 | 1718.8 |
| 192.7 | 640.3 | -411.6 | -2448.9 | -1242.7 | -732.7 | -43.6 | 223 | 51.3 | 1159.8 |
| 5519.4 | 1730.5 | -170.6 | 92.3 | -1518.4 | -250.2 | 454.9 | 594.8 | 1096.1 | 491.3 |
| 466.4 | 1061.5 | 1771.4 | 4451.6 | -1236.7 | 1743.8 | 524.7 | -18 | 0.3 | 298 |
| 1094.7 | 2638.5 | 5870.4 | 19499.6 | -1170.9 | 11810.1 | 206.9 | 1176.5 | 484.1 | 2903.3 |
| 96.2 | 794 | 2278.2 | 5264.6 | -1230.7 | 2730.6 | 20.7 | -16.5 | -50.2 | 1161.5 |
| 342.9 | -77.5 | -415.6 | -2598.4 | -1629.7 | -852.7 | -61.3 | 122.5 | 0.8 | 252.3 |
| 83.7 | 281.3 | -79.3 | 624.3 | -776.7 | 2799.1 | 246.4 | 152.3 | 149.6 | 1079.8 |
| 1238.4 | 638 | 272.9 | 1914.8 | 29.6 | 1111.1 | 325.7 | 1472.5 | 239.3 | 1255.5 |
| 520.7 | 220.5 | 288.9 | -72.4 | -671.2 | 561.1 | -44.8 | 237 | 358.1 | 864.8 |
| 1872.9 | -40.3 | -137.6 | -1654.4 | 2591.8 | -575.4 | 2097.2 | 1243.5 | 100.8 | 324.3 |
| 1822.2 | 32.8 | -325.6 | -2040.4 | -1493.7 | 5195.8 | 8.9 | 2193.3 | -47.4 | 980.8 |
| 965.7 | 2440.5 | 4650.4 | 22861.3 | -1376.2 | 7887.3 | 5111.2 | 861 | 252.3 | 554 |
| 716.2 | 1238 | 4486.2 | 20838.1 | -1079.7 | 5306.8 | 512.9 | 342.5 | 22.8 | 391.8 |
| 408.4 | 301.5 | 381.9 | 2591.3 | -726.9 | 5329.3 | -112.6 | 132 | 2.8 | 602.3 |
| 168.7 | 111 | -142.8 | -1335.9 | -1545.7 | -320.7 | -227.6 | 29 | 43.6 | 396.3 |

FIG. 1A

ASTHMA

| EGF (11) Fl - Bkgd | IL-5 (10) Fl - Bkgd | IL-4 (9) Fl - Bkgd | IL-1alpha (32) Fl - Bkgd | IL-7 (13) Fl - Bkgd | IL-6 (12) Fl - Bkgd | GM-CSF (39) Fl - Bkgd | IL-17 (30) Fl - Bkgd | IL-15 (28) Fl - Bkgd | TNF-alpha (40) Fl - Bkgd |
|---|---|---|---|---|---|---|---|---|---|
| 2847.5 | 1033.4 | -412.4 | -1689.5 | -1026.8 | -609.3 | 1311.1 | 310.9 | 6.8 | 570 |
| 1625.5 | -476.4 | -450.4 | -2153.3 | -1129.3 | -946.8 | 846.1 | -8.6 | -88.3 | -353 |
| 2796.3 | -289.4 | -166.1 | 807.5 | -1067.8 | -540.3 | 1024.6 | -15.6 | -77.3 | -400 |
| 2027.3 | -472.1 | -471.9 | -2030 | -1131.3 | -899.5 | 896.6 | -15.1 | -78.3 | -362 |
| 1584 | -434.9 | -507.9 | -1988.8 | -1114.8 | -948.5 | 912.1 | -26.4 | -84.8 | -333.5 |
| 516 | -401.9 | -473.4 | -1863.3 | -1108.8 | -848.8 | 553.1 | 109.9 | -82.3 | -391.8 |
| 2023 | -345.4 | -256.9 | -1662 | -945.5 | -625.5 | 1112.6 | 374.9 | 259.3 | 51.5 |
| 2625.5 | -310.6 | -254.4 | 315.3 | -1109 | -464 | 991.1 | -2.1 | -83.8 | -372.8 |
| 206 | -511.4 | -529.4 | -2130.5 | -1143 | -1000.8 | 984.6 | -48.1 | -93.3 | -384.3 |
| 2354.5 | -499.1 | -507.4 | -2171 | -1136.8 | -952 | 685.9 | -43.6 | -99.5 | -433.3 |
| 526 | -504.9 | -512.6 | -2104 | -1129.3 | -1017 | 992.4 | -42.9 | -104.8 | -439 |
| 3024.5 | 2746.4 | 5768.6 | 20978 | -1136.8 | 6980.3 | 1103.4 | -38.4 | -81.3 | -401.5 |
| 2141.3 | -21.1 | 361.6 | 3379.8 | -1128.3 | 264.8 | 742.1 | -27.4 | -98.3 | -397.5 |
| 799 | -466.6 | -470.1 | -2092.3 | -1143 | -1002.3 | 904.1 | -46.6 | -85.5 | -349.8 |
| 2297.8 | -494.6 | -501.9 | -1975.5 | -1136.3 | -960 | 983.1 | -33.6 | -80.3 | -424.5 |
| 1844.8 | -400.6 | -259.9 | -1549.3 | -1115.3 | -663.8 | 920.1 | -26.1 | -83.8 | -358.5 |
| 858.5 | -100.6 | 354.1 | -175.8 | -1121.8 | 138.3 | 385.4 | -8.9 | -94.3 | -394 |
| 1317.3 | -476.9 | -455.9 | -2008.8 | -1146.3 | -883 | 744.1 | -60.9 | -114.5 | -168.3 |
| 1858.8 | -492.9 | -500.6 | -2187 | -1122.5 | -1012.8 | 1025.1 | -48.6 | -104.5 | -453.3 |
| 1265.8 | -484.9 | -467.1 | -2049 | -1122.3 | -903.5 | 868.4 | -59.1 | -101.8 | -344 |
| 1315.3 | -488.4 | -501.4 | -2089 | -1125.5 | -961.3 | 698.9 | -41.4 | -105.8 | -439 |
| 1513.5 | -479.1 | -485.4 | -2097 | -1146.3 | -910.3 | 769.6 | -62.6 | -118 | -386.3 |
| 2084 | -505.1 | -511.9 | -1942.5 | -1075.8 | -973.8 | 855.6 | -50.6 | -118.5 | -351 |
| 1851 | -511.4 | -553.4 | -2120.3 | -1073.3 | -968 | 1555.1 | -48.1 | -133.5 | -468.3 |
| 1578 | 1051.9 | 2410.1 | 18496.5 | -1142.3 | 2644.8 | 885.4 | -61.6 | -113.8 | -440.3 |
| 879 | 494.1 | 1625.6 | 7695.8 | -1141 | 2169 | 914.6 | -13.6 | -102.8 | -383.3 |
| 1628 | -449.4 | -341.4 | -1980.3 | -1139.3 | -942.8 | 691.6 | -64.1 | -110.5 | -367 |
| 1533 | -318.4 | -419.9 | -2078 | -1115.8 | -925.3 | 819.6 | -23.6 | -92.5 | -291.5 |

| ASTHMA sE-Selectin (2) | EGF (11) | Leptin (31) | IL-5 (10) | PAI-1 (total) (84) | Resistin (61) | CRP (48) |
|---|---|---|---|---|---|---|
| Fl - Bkgd | Fl - Bkgd | Fl - Bkgd | Fl - Bkgd | Fl - Bkgd | Fl - Bkgd | Fl - Bkgd |
| 41.1 | 3057.7 | 4183.4 | 837.95 | -1331.5 | 180.3 | 1447.3 |
| 101.1 | 2414.2 | 25457.7 | -322.45 | -4967 | 451.3 | 5727.1 |
| 86.1 | 3646 | 15479.4 | 1673.8 | 1589.3 | 2800 | 11534.6 |
| 147.6 | 2453 | 5734.2 | 1654.1 | -3238.8 | 3251.3 | 23061.8 |
| 70.1 | 808.2 | 27786.4 | -277.95 | -3468 | 257.5 | 466.6 |
| 135.6 | 243.1 | 26296.4 | 5990.95 | -575.5 | 2198 | 23164.8 |
| 113.6 | 1936.45 | 23389.2 | -75.45 | -2620 | 5401.5 | 9192.8 |
| 70.4 | 2103.2 | 768.7 | 901.6 | -2637.3 | 244.3 | 4288.6 |
| 62.9 | 76.7 | 17499.7 | -327.85 | -4184.5 | -167.3 | 1794.3 |
| 215.6 | 4104.95 | 4991.7 | -283.05 | -2632.3 | 1475.5 | 5481.8 |
| 68.6 | 350.6 | 11771.7 | -314.95 | -3547.5 | -526.3 | 13526.3 |
| 222.4 | 5542.35 | 24368.4 | 4776.2 | -4380 | 4.8 | 26740.3 |
| 114.6 | 4137.75 | 24332.2 | 2651.95 | -1012.8 | 1583.8 | 27205.3 |
| 48.1 | 495.85 | 9072.7 | 86.85 | -3091 | 610.3 | 5778.8 |
| 198.4 | 3908.6 | 16031.2 | 617.95 | -3861 | 643.8 | 8300.3 |
| 177.1 | 1155.6 | 28179.7 | 330.45 | -4505.8 | 1248.3 | 23909.3 |
| 75.1 | 976.6 | 8057.2 | 1268.95 | -4153 | -67 | 3170.3 |
| 119.6 | 706.75 | 23356.7 | 158.55 | -3918 | 91 | 23915.3 |
| 127.6 | 1100.85 | 7960.7 | -285.2 | -3215.5 | 1468.8 | 13231.8 |
| 84.6 | 674.75 | 25997.4 | -101.8 | -3147.3 | 1447 | 15755.8 |
| 64.4 | 1276.85 | 24228.7 | 74.8 | -249 | 293.3 | 13192.8 |
| 105.6 | 1017.25 | 23020.7 | -129.3 | -1114.5 | 1358.3 | 3380.3 |
| 97.9 | 1978.45 | 24345.2 | -272.7 | -2795.8 | 3661.5 | 15276.3 |
| 74.1 | 1836.6 | 18608.7 | -239.3 | -4170.5 | 343 | 7091.8 |
| 140.1 | 1271.85 | 26408.4 | 1746.2 | -5449.5 | -77.5 | 22101.8 |
| 49.6 | 797.6 | 10468.7 | 866.05 | -2863.8 | 969 | 1649.8 |
| 71.1 | 1018.2 | 6210.7 | -73.95 | -1418 | 714 | 24262.6 |
| 106.6 | 850.85 | 26654.2 | -103.7 | -1894.5 | 1320.5 | 2809.6 |
| Ave 106.7714286 | 1641.404085 | 17523.57143 | 697.021614 | -2816.182143 | 1113.535714 | 12052.07857 |
| Stdev 49.48371118 | 1601.461118 | 8823.115523 | 2155.595968 | 1591.944635 | 1337.701062 | 8985.625664 |
| RSD 46.34546137 | 97.56653666 | 50.34998464 | 309.2581241 | -56.52846849 | 120.1309527 | 74.55664689 |

FIG. 2B

| ASTHMA | | | | | | |
|---|---|---|---|---|---|---|
| MMP-9 (47) | IL-4 (9) | IL-1alpha (32) | SAA (67) | IL-7 (13) | IL-6 (12) | MMP-13 (66) |
| Fl - Bkgd | Fl - Bkgd | Fl - Bkgd | Fl - Bkgd | Fl - Bkgd | Fl - Bkgd | Fl - Bkgd |
| 28520.7 | -226.85 | -125.95 | 140.3 | -1259.35 | 1091 | 3.4 |
| 29867.9 | -396.75 | -2307.85 | 631 | -1248.85 | 201.5 | 1.7 |
| 29813.9 | 1010.8 | 8596.8 | 539.5 | -330.85 | 1570 | 3.7 |
| 29505.2 | 3645.75 | 9249.3 | 3021.8 | -1197 | 7170.15 | 8.7 |
| 29752.2 | -307.6 | -745.5 | 110.3 | -1317.6 | -641.6 | 0.7 |
| 26426.9 | 6504.65 | -1664.35 | 1251.5 | 2808.25 | 8144.9 | 4.7 |
| 28919.2 | -121.85 | -1319.2 | 1021.8 | -784.1 | 2170.55 | 20.2 |
| 28812.2 | 838 | 9093.55 | 1043.3 | -1078.95 | 1478.9 | 10.4 |
| 28796.7 | -177.25 | -2246.7 | 242.8 | -1154.1 | -903.75 | 6.7 |
| 29618.7 | -407 | -1960.35 | 795.8 | -747.5 | 176.4 | 11.2 |
| 28577.4 | -483.35 | -2354.2 | 906.3 | -714.1 | -926.35 | 3.7 |
| 28431.2 | 9159.75 | 23028.8 | 5518.5 | -1314.5 | 12526.05 | -2.1 |
| 28909.4 | 5723.15 | 12724.2 | 5739 | -1156.85 | 10106.2 | 2.2 |
| 28299.7 | -440.85 | -2270.6 | 320.3 | -1192.85 | -867.5 | 1.4 |
| 27687.2 | -336.25 | -941.6 | 1337.5 | -1332.35 | -605.1 | 4.4 |
| 28207.4 | 755.75 | 1451.15 | 2716.5 | -1176 | 540 | 3.7 |
| 28386.2 | 3112.25 | 9661.9 | 370.8 | -1146.35 | 5974.2 | 5.2 |
| 29621.7 | 911.15 | 1627.9 | 756.8 | -1188.5 | 923.8 | 2.2 |
| 27408.2 | -458.1 | -2392.7 | 399 | -1390.85 | -932.75 | 6.4 |
| 28079.4 | -273.2 | -712.35 | 492.3 | -949.6 | 947.8 | 3.9 |
| 29659.2 | -114.25 | -87.1 | 1565.3 | -547.95 | 74.9 | 3.4 |
| 28087.2 | -98.25 | -1084.7 | 275.5 | -908.75 | -174.6 | 1.7 |
| 27261.2 | -324.75 | -1798.45 | 710.8 | 758 | -774.6 | 0.7 |
| 28586.9 | -439.5 | -2080.35 | 2855 | -1283.5 | 2113.9 | 2.2 |
| 26646.4 | 3530.25 | 20678.9 | 3010.5 | -1259.25 | 5266.05 | 1.7 |
| 29078.2 | 3055.9 | 14266.95 | 362.3 | -1110.35 | 3737.9 | 2.9 |
| 28019.7 | 20.25 | 305.5 | 803.3 | -933.1 | 2193.25 | -1.8 |
| 28691.9 | -281.35 | -1706.95 | 2686.8 | -1330.75 | -623 | -2.8 |
| Ave 28559.7179 | 1161.138755 | 2721.618634 | 1415.164286 | -808.7637262 | 1959.110038 | 3.942857143 |
| Stdev 916.631172 | 3181.881387 | 8088.311223 | 1503.119905 | 1241.922129 | 4889.964841 | 4.577758514 |
| RSD 3.20952461 | 274.0311073 | 297.1875681 | 106.2152232 | -153.5580899 | 249.6013367 | 116.102571 |

FIG. 2C

ASTHMA

| CD40 Ligand (18) | sVCAM-1 (16) | HGF (53) | C-Peptide (73) | sICAM-1 (24) | MMP-7 (30) | Adiponectin (51) |
|---|---|---|---|---|---|---|
| Fl - Bkgd | Fl - Bkgd | Fl - Bkgd | Fl - Bkgd | Fl - Bkgd | Fl - Bkgd | Fl - Bkgd |
| 1541 | 3358.2 | 881 | 24700.2 | 4000.4 | 390.8 | 22344.6 |
| 1279.5 | 3704.2 | 1392 | 26033.7 | 4747.6 | 455.8 | 22886.6 |
| 1250.5 | 3956.7 | 2050.8 | 27879.7 | 15793.1 | 325.8 | 22975.1 |
| 1255.3 | 4324.9 | 1212 | 18550.2 | 5727.9 | 482.8 | 21394.1 |
| 212.5 | 3372.2 | 115.3 | 26293.9 | 3381.4 | 299.3 | 24217.1 |
| 319.5 | 6140.7 | 667 | 19362.2 | 8821.4 | 699.8 | 22064.6 |
| 882 | 3251.2 | 724.5 | 19672.2 | 4281.6 | 487.3 | 20227.4 |
| 937.8 | 3443.7 | 457 | 21307.2 | 3258.6 | 335.1 | 22621.4 |
| 283.5 | 2702.2 | 673 | 13613.4 | 3190.4 | 528.8 | 22967.1 |
| 1104.8 | 3370.4 | 2043.5 | 22269.2 | 5592.1 | 160.6 | 18885.6 |
| 1487.3 | 3355.4 | 741 | 26167.9 | 3583.4 | 311.3 | 21303.1 |
| 230 | 4621.7 | 748.3 | 8491.9 | 6938.9 | 549.3 | 18567.6 |
| 431.3 | 3210.2 | 767.5 | 23553.9 | 4991.1 | 447.1 | 21988.4 |
| 270 | 4087.7 | 623.8 | 25802.4 | 3073.6 | 273.8 | 22402.4 |
| 1156.3 | 3654.2 | 427.5 | 22875.2 | 5387.9 | 631.3 | 21471.1 |
| 209 | 5003.7 | 1304 | 18392.9 | 6536.4 | 385.8 | 23256.6 |
| 537.5 | 5672.2 | 774.5 | 12550.2 | 4612.1 | 365.3 | 23492.6 |
| 282.3 | 3528.2 | 1570 | 27912.9 | 4455.4 | 424.8 | 13223.6 |
| 427.5 | 3358.2 | 592.5 | 24690.7 | 5120.4 | 472.3 | 23201.4 |
| 503 | 2660.2 | 926.5 | 25388.4 | 2642.4 | 382.8 | 23333.1 |
| 1428.5 | 3407.2 | 1344.5 | 25576.7 | 2957.4 | 247.3 | 15552.1 |
| 822 | 3774.9 | 652.5 | 26310.2 | 4735.9 | 161.3 | 22040.1 |
| 478 | 3041.7 | 395.5 | 22629.7 | 5248.6 | 580.8 | 24682.9 |
| 1068.5 | 4310.7 | 791 | 20430.7 | 4771.9 | 215.8 | 21392.1 |
| 124.5 | 5136.4 | 738.5 | 13373.4 | 5009.9 | 383.3 | 10991.1 |
| 309 | 3166.2 | 776.3 | 18309.4 | 4448.6 | 216.1 | 23094.1 |
| 506 | 3026.2 | 896.3 | 18326.9 | 3411.9 | 327.8 | 21974.9 |
| 354.5 | 3324.7 | 1038.8 | 17446.7 | 4391.9 | 265.3 | 22222.6 |
| 703.2714286 | 3784.432143 | 904.4678571 | 21354 | 5039.721429 | 385.9857143 | 21241.90714 |
| 459.3268431 | 856.9428963 | 455.1834266 | 5055.30836 | 2494.409549 | 137.3736584 | 3183.073367 |
| 65.31288268 | 22.64389647 | 50.32610314 | 23.67382392 | 49.49498864 | 35.59034785 | 14.98487563 |

Ave
Stdev
RSD

FIG. 2D

| ASTHMA GM-CSF (39) Fl - Bkgd | IL-17 (30) Fl - Bkgd | IL-15 (28) Fl - Bkgd | MMP-12 (62) Fl - Bkgd | TNF-alpha (40) Fl - Bkgd | I-TAC (60) Fl - Bkgd | MIF (41) Fl - Bkgd |
|---|---|---|---|---|---|---|
| 704.75 | 935.7 | 9.55 | 0.9 | 750.9 | 20.7 | 134 |
| 855 | 364.7 | 8 | 1.9 | 137.5 | 33.7 | 145.5 |
| 1716.5 | 558.45 | 251.5 | -1.8 | -87.75 | 12.2 | 399.8 |
| 763.15 | 1773.45 | 53.25 | 0.4 | 856.4 | 22.2 | 82.3 |
| 361.75 | -24.95 | -61.5 | -0.1 | -109.5 | 14.7 | 147.5 |
| 238 | 4732.35 | -16.75 | 2.7 | 5.5 | 30.9 | 177 |
| 746.75 | 2258.35 | 346.3 | 7.9 | 2084.75 | 15.7 | 285 |
| 843.15 | -22.2 | -45.35 | 4.4 | 30.25 | 10.9 | 118.8 |
| 499 | -23.15 | -59 | -5.1 | 15.85 | 12.4 | 43.5 |
| 766.55 | 264.95 | 425.15 | -0.6 | 210 | 37.9 | 78 |
| 594.9 | -31.7 | -39.5 | 0.4 | 65.5 | 20.2 | 130.8 |
| 987.4 | 106.05 | -33.75 | 1.4 | 36.4 | 61.7 | 174.5 |
| 528.75 | 2739.8 | 169.25 | -2.6 | 660.65 | 18.2 | 180 |
| 430.25 | 88.2 | -17.1 | -3.8 | 405 | 11.2 | 82.3 |
| 719 | 280.6 | 507.9 | -1.1 | 33.4 | 13.7 | 134 |
| 722.4 | -22.05 | -41.75 | 2.4 | -30.25 | 44.2 | 109.5 |
| 296.15 | 583.8 | 194.9 | -2.8 | 1254.65 | 11.2 | 74 |
| 382.4 | -38.7 | -82.35 | -4.6 | 496.6 | 17.2 | 77.8 |
| 481.9 | 36.95 | -51.85 | -1.6 | -100.5 | 24.7 | 154 |
| 557.4 | 46.6 | 23.9 | -1.8 | 367.9 | 18.2 | 109 |
| 512.3 | 715.55 | 66.75 | -2.1 | 408.25 | 7.7 | 170.8 |
| 362.4 | 87.2 | 120.05 | -1.1 | 239.25 | 10.2 | 108.5 |
| 1476.4 | 596.45 | -8.85 | 0.9 | -13.35 | 27.9 | 250.5 |
| 782 | 1072.6 | -90.45 | 0.9 | 256.25 | 26.2 | 95 |
| 2998.3 | 399.7 | 69.25 | -6.6 | 56.85 | 10.7 | 285 |
| 713.75 | 164.45 | -40 | -2.6 | 4.25 | 11.9 | 60.5 |
| 289.5 | 33.95 | -53.85 | -3.1 | 117.65 | 18.4 | 88.5 |
| 296 | 2.7 | -24.45 | -7.3 | 52.4 | 16.7 | 122 |
| 710.814118 | 579.9204111 | 53.04178098 | -0.875 | 262.5852043 | 20.76785714 | 143.5035714 |
| 764.4823081 | 1578.182212 | 248.1581354 | 3.262426386 | 869.1080302 | 12.0692463 | 79.26835099 |
| 107.5502426 | 272.1377089 | 467.8540781 | -372.8487299 | 330.9813409 | 58.1150295 | 55.23789422 |

Ave
Stdev
RSD

NORMAL

| EGF (11) Fl - Bkgd | IL-5 (10) Fl - Bkgd | IL-4 (9) Fl - Bkgd | IL-1alpha (32) Fl - Bkgd | IL-7 (13) Fl - Bkgd | IL-6 (12) Fl - Bkgd | GM-CSF (39) Fl - Bkgd | IL-17 (30) Fl - Bkgd | IL-15 (28) Fl - Bkgd | TNF-alpha (40) Fl - Bkgd |
|---|---|---|---|---|---|---|---|---|---|
| 1270.5 | -340.3 | 1707.3 | 11009.5 | 1497.5 | 1283.8 | -401 | 1184.3 | 18.3 | 250.5 |
| 2398.8 | -1384.5 | -221.8 | -2538 | -1555.5 | -940 | 260.5 | -23.5 | 161 | 831.8 |
| 8004.3 | 1636 | 5090.8 | 20164.5 | -1610 | 9720 | 596 | 3291.5 | -12 | 232.5 |
| 7620 | 3006 | 7102.3 | 16477.5 | 1900.8 | 5730.3 | 3427.8 | 2953.5 | 3516 | 3220 |
| 3538 | 356 | 5053.3 | 21193.8 | 5158.5 | 7052 | -199.8 | 92.3 | 52.5 | 231 |
| 2029.8 | 68.8 | 3126 | 8510 | -1949 | 2973.5 | -329 | 382.5 | 294 | 282.5 |
| 7842.5 | -1158.3 | 144.5 | -2228.3 | 2116.5 | -888 | -276.8 | -134.5 | 509.3 | -99.8 |
| 16536.5 | 381.8 | 1412.8 | 13813.8 | -1290 | 6833.5 | 692.3 | 4442.5 | 22.3 | 1265.5 |
| 12483 | 1295 | 3890.3 | 21678.5 | -208.3 | 23454.3 | 3433.5 | 21116 | 700.5 | 17370 |
| 3914.5 | -1290 | 561.5 | -2991.3 | -1852.5 | -828.5 | -185 | -140.8 | 4 | -142.5 |
| 9296.5 | -1317.5 | -85.5 | -2940.8 | -1673.5 | -1147.8 | -332.8 | 267 | 20.5 | 19.8 |
| 12540 | -1436.5 | -329 | -3005.3 | -1969.8 | -955.5 | -196.3 | 148 | -65 | -189 |
| 5425.5 | -1247.5 | 149.3 | -1305.8 | -1945 | -461.3 | -384 | -7.5 | -125.5 | 258.5 |
| 773.8 | -1416.8 | -65.5 | -3126.5 | -1985 | -1253 | -560.8 | -216 | -99.5 | -425.8 |
| 1437 | 462.8 | 3456.8 | 15963.8 | -1164.5 | 4813 | 871 | -21.3 | 576.5 | 377.5 |
| 5387.5 | -1334.5 | -411.8 | -2846 | -1765.3 | -1159.5 | -483.5 | -115 | -74.8 | -462.3 |
| 3057.5 | -1040 | 30 | -2894.8 | -1488 | -1100 | -425.5 | -187.3 | 158.8 | 540.8 |
| 2462.8 | -1369.5 | -141.5 | -2703.8 | -1286.3 | -1204.8 | -396 | -35.5 | -33 | 179.5 |
| 1583.5 | 899.8 | 6517.8 | 17422.8 | -1786.3 | 10469 | 265 | 483.5 | -68.8 | -354.5 |
| 1616 | 2322.5 | 10304.3 | 23281.8 | -1694 | 13553.5 | 221 | -240 | -98.5 | -178.5 |
| 337 | -1311 | 91 | -1858 | -1454.5 | -542.5 | -294.8 | -34.5 | -33.8 | -18.5 |
| 15241.5 | -44.5 | 4170.3 | 16341.5 | -1822 | 4747.5 | 14 | -201.3 | 112.3 | 93.5 |
| 5755.5 | -1354.8 | -336.5 | 1111.3 | -1290.3 | -546.5 | -554 | 77.8 | -93.8 | -357.5 |
| 5484.3 | 153.8 | 532 | 2265.8 | -1956.8 | 2599.8 | -122.8 | 71.5 | -55.3 | -38 |
| 5032 | -703.8 | 4072.5 | -707.5 | 1642 | 97322.5 | -223.8 | 9348.5 | 1061 | 9486.8 |
| 3553.5 | -538.8 | 2252.5 | -2862.8 | -265.5 | 2253 | 421 | 3278.8 | 376.8 | 2974.8 |
| 207.8 | -659.5 | 2247.3 | 11941.3 | -1836 | 1319 | -158.8 | -124.5 | -42.8 | 184.5 |
| 3916.5 | 407.8 | 5384.8 | 20747.5 | 7201.3 | 7647 | -163.3 | 359.3 | 245 | 498.5 |
| 500.5 | -1460.3 | 356.8 | -2720.5 | -1923.5 | 3076.3 | -178 | 4097.5 | -80.8 | -239.5 |
| 1227.5 | -394.8 | 1769.5 | 10029.8 | -343.8 | 507.5 | -376 | 309 | 14.3 | -215.3 |

FIG. 3A

| NORMAL | | | | | | | | | |
|---|---|---|---|---|---|---|---|---|---|
| EGF (11) | IL-5 (10) | IL-4 (9) | IL-1alpha (32) | IL-7 (13) | IL-6 (12) | GM-CSF (39) | IL-17 (30) | IL-15 (28) | TNF-alpha (40) |
| FI - Bkgd | FI - Bkgd | FI - Bkgd | FI - Bkgd | FI - Bkgd | FI - Bkgd | FI - Bkgd | FI - Bkgd | FI - Bkgd | FI - Bkgd |
| 1989.3 | 611 | 94.3 | -85.1 | -1129 | -258.1 | 1050.1 | 169.4 | -32.3 | 130.5 |
| 1894.3 | -294.5 | 234.8 | -2557.6 | -1151 | -951.9 | 919.4 | 26.9 | -71 | -196.8 |
| 2053.8 | -352.5 | 349.5 | -2546.1 | -1153.5 | -943.9 | 700.4 | -34.6 | -115 | -347.3 |
| 1807.5 | -151 | 554 | -386.1 | -1127.5 | -338.1 | 523.4 | 14.1 | -64.5 | -324.5 |
| 2135.5 | -373 | -141.8 | -1985.1 | -1153.5 | -844.1 | 779.1 | -36.9 | -95.5 | -403.8 |
| 1717 | -326 | -103 | -1834.1 | -1150.5 | -618.6 | -491.9 | -36.1 | -106.8 | -348.3 |
| 2064.5 | -348 | 220 | -2205.9 | -1118.5 | -816.9 | 15.6 | -53.1 | -113.8 | -350 |
| 2391 | -357.8 | 267 | -2413.6 | -1109.5 | -948.9 | 750.6 | -60.4 | -168.8 | -328.3 |
| 2010.5 | -248.3 | 198 | 143.6 | -1155 | 15.4 | 932.1 | 24.1 | -111.3 | -349.3 |
| 2254.8 | -416 | 1069.3 | -2730.1 | -1168.5 | -1014.6 | 1067.6 | -59.4 | -119.8 | -392 |
| 2705 | -428 | 157.5 | -2599.9 | -1155.5 | -1013.9 | 827.9 | -34.4 | -103 | -368 |
| 1974.3 | -420.5 | -248.5 | -2656.9 | -1143.8 | -1028.1 | 790.4 | -46.4 | -121 | -412.8 |
| 2440.8 | -415.8 | -171.5 | -2578.1 | -1148.5 | -1001.4 | 870.4 | -46.9 | -123.8 | -317 |
| 1284.8 | -428.3 | 818 | -2690.1 | -1164.8 | -1036.6 | 691.4 | -66.4 | -140.5 | -442.3 |
| 1581 | -327 | -143 | -998.1 | -1159.5 | -666.6 | 709.6 | -39.9 | -97.3 | -404.5 |
| 1965 | -414.8 | -312 | -2706.4 | -1118.5 | -994.6 | 716.6 | 4.6 | -81.3 | -220.5 |
| 1305.5 | -412.5 | 51 | -2719.9 | -1159.3 | -981.4 | 547.4 | -56.4 | -122.3 | -371.8 |
| 2259.5 | -428.8 | 74.8 | -2612.6 | -1152 | -1028.4 | 571.6 | -34.4 | -99.3 | -384.3 |
| 1236.3 | -353.5 | 1316 | -2204.4 | -1165.5 | -783.9 | 493.1 | -40.9 | -106.3 | -420.3 |
| 1150.3 | -235 | 79 | 1066.4 | -1152.3 | -204.1 | 875.1 | -48.1 | -107.8 | -377.5 |
| 842.3 | -426.5 | 13.8 | -2652.6 | -1162.5 | -1017.6 | 719.6 | -37.6 | -124.8 | -422 |
| 1661 | -353.5 | -114.5 | -1686.9 | -1166 | -799.4 | 842.6 | -34.9 | -115.3 | -419 |
| 1755.5 | -428 | -153.8 | -2666.1 | -1161.8 | -1007.9 | -403.1 | -36.4 | -121.3 | -357.8 |
| 1721.8 | -226.5 | -39.5 | 203.4 | -1149 | -250.9 | 762.6 | -31.4 | -114.8 | -331.8 |
| 2238.5 | -413 | -305.8 | -2650.6 | -1148.5 | -990.6 | 457.4 | -11.9 | -97 | -363.8 |
| 1566 | -421.8 | 635.8 | -2651.1 | -1161 | -1015.6 | 501.1 | -41.4 | -105 | -410.3 |
| 1270 | -281.8 | 68.8 | -393.9 | -1160.5 | -521.6 | 683.6 | -12.6 | -110.3 | -398.8 |
| 1935.5 | -373.5 | -114.5 | -2005.6 | -1165.5 | -869.4 | 734.4 | -65.4 | -119.8 | -400.8 |
| 1355.5 | -431.3 | 106 | -2618.1 | -1169.8 | -1020.9 | 998.1 | -21.1 | -117 | -430.5 |
| 1683 | -329.3 | -477 | 128.4 | -1154 | -706.1 | 691.6 | -24.6 | -106.3 | -349.3 |
| | | -261.8 | | | | | | | |

NORMAL

| sE-Selectin (2) | EGF (11) | Leptin (31) | IL-5 (10) | PAI-1 (total) (84) | Resistin (61) | CRP (48) |
|---|---|---|---|---|---|---|
| FI - Bkgd | FI - Bkgd | FI - Bkgd | FI - Bkgd | FI - Bkgd | FI - Bkgd | FI - Bkgd |
| -3763.3 | 1629.9 | 7415.9 | 135.35 | 6066.5 | 2770.5 | 4603.5 |
| -3720.3 | 2146.55 | -1191.9 | -839.5 | 5389.5 | 5651.5 | 7744.8 |
| -3775.1 | 5029.05 | 43.1 | 641.75 | 4444.3 | 1509 | 2310.5 |
| -3756.8 | 4713.75 | -1236.4 | 1427.5 | 4936.8 | 8428.8 | 3325 |
| -3788.6 | 2836.75 | 8182.4 | -8.5 | 7063.8 | 2132.8 | 24163.3 |
| -3777.8 | 1873.4 | 7054.6 | -128.6 | 5841 | 5540.8 | 8198.3 |
| -3772.1 | 4953.5 | 5812.1 | -753.15 | 3889 | 1904 | 10043 |
| -3705.8 | 9463.75 | 928.6 | 12 | 5574.5 | 11272.5 | 14322 |
| -3749.6 | 7246.75 | 23106.9 | 523.35 | 3931 | 2942.5 | 650 |
| -3759.6 | 3084.65 | 2390.4 | -853 | 3642.3 | 1665 | 3330.5 |
| -3752.3 | 6000.75 | 21581.4 | -872.75 | 3086.8 | 4458.5 | 11344.5 |
| -3705.8 | 7257.15 | 24406.9 | -928.5 | 3947 | 3228.3 | 27124.5 |
| -3712.3 | 3933.15 | 2033.6 | -831.65 | 3539.8 | 1824.5 | 4497.3 |
| -3771.6 | 1029.3 | 11804.1 | -922.55 | 5105.8 | 2416.8 | 24720.5 |
| -3731.1 | 1509 | -1317.6 | 67.9 | 3725 | 5043.8 | 5733.5 |
| -3763.8 | 3676.25 | 4805.6 | -874.65 | 3120 | 2967.8 | 4766 |
| -3794.1 | 2181.5 | 20704.4 | -726.25 | 5027 | 3201.3 | 22934 |
| -3759.3 | 2361.15 | 23092.9 | -899.15 | 2431.8 | 1236.3 | 9247.8 |
| -3774.3 | 1409.9 | 1522.6 | 273.15 | 5300.3 | 3528.5 | 8471.3 |
| -3761.8 | 1383.15 | 6621.1 | 1043.75 | 3415.3 | 2863 | 5033.3 |
| -3780.8 | 589.65 | 20321.6 | -868.75 | 5036.5 | 3023.3 | 23052 |
| -3645.6 | 8451.25 | 15493.4 | -199 | 2472 | 1567 | 742 |
| -3695.6 | 3755.5 | -1787.6 | -891.4 | 4632.5 | 2777.8 | 7165.8 |
| -3787.6 | 3603.05 | 21040.4 | -36.35 | 3806.5 | 3159 | 24177.3 |
| -3774.8 | 3635.25 | 15915.9 | -558.4 | 6572.5 | 1743 | 27071.5 |
| -3775.8 | 2559.75 | 6621.1 | -480.3 | 5426 | 1897.8 | 3974.5 |
| -3770.8 | 738.9 | 20321.6 | -470.8 | 4899.5 | 1061 | 2205.5 |
| -3712.6 | 2926 | 6395.9 | 17.15 | 7743.5 | 935.8 | 5670 |
| -3791.8 | 927.9 | 164.9 | -945.8 | 4704.5 | 1513 | 7101.3 |
| -3789.3 | 1455.25 | 124.9 | -362.05 | 4730.5 | 1876.8 | 3596 |
| Ave -3754.003333 | 3304.775174 | 8089.08 | -356.5528724 | 24525.83333 | 3138.023333 | 10243.98333 |
| Stdev 35.15090113 | 3481.125588 | 9137.49273 | 709.5513187 | 1290.903257 | 2234.37791 | 8699.538503 |
| RSD -0.93635775 | 105.3362303 | 112.9608402 | -199.0031139 | 5.263442998 | 71.20335551 | 84.92339571 |

FIG. 4B

| NORMAL | | | | | | |
|---|---|---|---|---|---|---|
| MMP-9 (47) | IL-4 (9) | IL-1alpha (32) | SAA (67) | IL-7 (13) | IL-6 (12) | MMP-13 (66) |
| Fl - Bkgd | Fl - Bkgd | Fl - Bkgd | Fl - Bkgd | Fl - Bkgd | Fl - Bkgd | Fl - Bkgd |
| 29261.5 | 900.8 | 5462.2 | 205.8 | 184.25 | 512.85 | 2.8 |
| 28703 | 6.5 | -2547.8 | 1700 | -1353.25 | -945.95 | -1.8 |
| 29460.3 | 2720.15 | 8809.2 | 202 | -1381.75 | 4388.05 | 5.8 |
| 28239.3 | 3828.15 | 8045.7 | 597 | 386.65 | 2696.1 | -2.5 |
| 28919.5 | 2455.75 | 9604.35 | 988.5 | 2002.5 | 3103.95 | 0.3 |
| 27819.8 | 1511.5 | 3337.95 | 1960.5 | -1549.75 | 1177.45 | 0.3 |
| 29306.8 | 182.25 | -2217.1 | 392.3 | 499 | -852.45 | -4.8 |
| 28981.8 | 839.9 | 5700.1 | 535.3 | -1199.75 | 2942.3 | -9.3 |
| 28374 | 2044.15 | 10911.05 | 75.5 | -681.65 | 11734.85 | 1.5 |
| 27820 | 815.4 | -2860.7 | 1818.3 | -1510.5 | -921.55 | -4 |
| 27425.3 | 36 | -2770.35 | 133.5 | -1414.5 | -1080.85 | -1.3 |
| 27772 | -288.75 | -2831.1 | 23490.5 | -1556.8 | -991.8 | -0.8 |
| 27442.5 | -11.1 | -1941.95 | 266 | -1546.75 | -731.35 | 4.8 |
| 28065.3 | 376.25 | -2908.3 | 1130 | -1574.9 | -1144.8 | -2.3 |
| 29720 | 1656.9 | 7482.85 | 1467 | -1162 | 2073.2 | 3.3 |
| 27010.3 | -361.9 | -2776.2 | 218 | -1441.9 | -1077.05 | -2.3 |
| 29315.8 | 40.5 | -2807.35 | 1174 | -1323.65 | -1040.7 | -2.3 |
| 29190.3 | -33.35 | -2658.2 | 2161 | -1219.15 | -1116.6 | -1.8 |
| 29209.5 | 3916.9 | 7609.2 | 233 | -1475.9 | 4842.55 | -2.3 |
| 28616.5 | 5191.65 | 12174.1 | 404.5 | -1423.15 | 6674.7 | -2.3 |
| 28872.3 | 52.4 | -2255.3 | 508 | -1308.5 | -780.05 | 5.8 |
| 28820.8 | 2008.25 | 7327.3 | 67.5 | -1494 | 1974.05 | 28.5 |
| 29598.8 | -188 | -777.4 | 126.5 | -1226.05 | -777.2 | -2.3 |
| 28908 | 113.1 | 1234.6 | 2964.8 | -1552.9 | 1174.45 | 3 |
| 28887 | 2354.15 | -1679.05 | 2443 | 246.75 | 4370.95 | 1.5 |
| 27094 | 1160.65 | -2756.95 | 162.8 | -713.25 | 618.7 | -5.5 |
| 26869.3 | 1066.4 | 5773.7 | 251.5 | -1498.25 | 398.7 | -1.8 |
| 28665.5 | 2745.4 | 9370.95 | 334.3 | 3017.9 | 3388.8 | -3.8 |
| 28823.8 | -60.1 | -2669.3 | 110 | -1546.65 | 1027.7 | 4 |
| 29024.5 | 753.85 | 5079.1 | 136.5 | -748.9 | -99.3 | -1.5 |
| Ave 28540.58333 | 1069.536209 | 1939.187411 | 1541.92 | -849.1320211 | 1299.467541 | 0.296666667 |
| Stdev 803.6366468 | 2037.999356 | 7624.963837 | 4224.236492 | 1576.802446 | 4447.770372 | 6.354063773 |
| RSD 2.81576812 | 190.5498233 | 393.2040706 | 273.959511 | -185.6957936 | 342.2763733 | 2141.819249 |

FIG. 4C

| NORMAL | | | | | | | |
|---|---|---|---|---|---|---|---|
| CD40 Ligand (18) | sVCAM-1 (16) | HGF (53) | C-Peptide (73) | sICAM-1 (24) | MMP-7 (30) | Adiponectin (51) | |
| Fl - Bkgd | Fl - Bkgd | Fl - Bkgd | Fl - Bkgd | Fl - Bkgd | Fl - Bkgd | Fl - Bkgd | |
| 346.9 | 183.9 | 612.4 | 818.5 | -4397.4 | 287.4 | 20953.1 | |
| 286.4 | 2399.4 | 568.6 | 7261.5 | -3029.4 | 284.4 | 24645.4 | |
| 674.4 | 1564.2 | 1097.9 | 1013.5 | -3778.4 | 260.9 | 23757.9 | |
| 166.9 | 2404.2 | 400.1 | 3123 | -2069.4 | 400.4 | 25081.1 | |
| 223.1 | 713.9 | 1107.4 | 17376.8 | -4337.4 | 319.6 | 22526.4 | |
| 40.1 | 1259.7 | 652.4 | 15973.5 | -3921.9 | 338.1 | 24778.9 | |
| -5.4 | 671.4 | 692.9 | 102 | -4959.4 | 203.4 | 23652.9 | |
| 64.1 | 897.9 | 185.4 | 9121.5 | -534.1 | 382.1 | 25697.9 | |
| 4.1 | 937.9 | 557.4 | 26009.5 | -4181.9 | 397.6 | 25126.6 | |
| 83.4 | 313.4 | 304.4 | 562.3 | -5952.4 | 384.4 | 24955.6 | |
| -18.1 | 636.7 | 762.4 | 1171.3 | -4046.1 | 243.4 | 24441.6 | |
| 161.4 | 1398.7 | 627.9 | 311 | -2086.4 | 212.6 | 25066.4 | |
| 691.9 | 379.7 | 1037.9 | 1454.3 | -2547.9 | 302.4 | 24909.1 | |
| 105.9 | 212.9 | 360.4 | 780.5 | -3811.1 | 260.4 | 25380.1 | |
| 218.9 | 2024.4 | 706.4 | 2421.8 | -3371.6 | 226.4 | 24860.1 | |
| 36.4 | 627.2 | 620.1 | 10812.3 | -4418.6 | 569.4 | 25360.9 | |
| 253.4 | 282.2 | 1661.4 | 14363 | -5488.6 | 282.4 | 23958.9 | |
| -31.6 | 1053.9 | 1217.9 | 24882 | -4148.9 | 407.9 | 25347.9 | |
| 28.9 | 351.9 | 517.9 | 4614 | -5359.6 | 260.1 | 24671.4 | |
| 67.9 | 875.9 | 178.4 | 23592.8 | -5744.9 | 316.1 | 24751.1 | |
| -42.1 | 1097.4 | 316.9 | 21762.8 | 970.4 | 239.4 | 24203.9 | |
| 69.4 | 1507.4 | 1199.9 | 4378.5 | -2372.9 | 260.9 | 25686.1 | |
| 5.6 | 886.9 | 769.9 | 1965.5 | -856.4 | 383.1 | 24569.1 | |
| 208.1 | 894.4 | 906.9 | 8969 | -4280.1 | 250.4 | 24436.6 | |
| 405.1 | 1742.7 | 1254.4 | 16084 | -592.9 | 220.4 | 25519.1 | |
| -9.1 | 642.9 | 401.1 | 2880.5 | -1157.6 | 418.6 | 24306.9 | |
| -41.6 | 1637.7 | 244.9 | 19516.5 | -4690.9 | 468.1 | 26178.1 | |
| 186.6 | 720.7 | 780.6 | 8190.8 | -2396.4 | 273.6 | 25731.4 | |
| 338.4 | 785.4 | -127.4 | 11127 | -5811.4 | 210.6 | 24937.9 | |
| 316.6 | 1427.4 | -116.6 | 1407 | -5270.9 | 209.1 | 20282.6 | |
| 161.2 | 1017.743333 | 650.0066667 | 8734.89 | -3488.15 | 309.12 | 24525.83333 | Ave |
| 192.0483955 | 609.3685356 | 413.4388959 | 8388.217319 | 1784.703995 | 88.75857763 | 1290.903257 | Stdev |
| 119.1367218 | 59.87448069 | 63.60533162 | 96.03117291 | -51.16477202 | 28.71330798 | 5.263442998 | RSD |

FIG. 4D

| NORMAL GM-CSF (39) Fl - Bkgd | IL-17 (30) Fl - Bkgd | IL-15 (28) Fl - Bkgd | MMP-12 (62) Fl - Bkgd | TNF-alpha (40) Fl - Bkgd | I-TAC (60) Fl - Bkgd | MIF (41) Fl - Bkgd |
|---|---|---|---|---|---|---|
| 324.55 | 676.85 | -7 | -2.6 | 190.5 | 16.9 | 88.3 |
| 589.95 | 1.7 | 45 | -0.6 | 317.5 | 155.4 | 83 |
| 648.2 | 1628.45 | -63.5 | 0.4 | -57.4 | 16.2 | 75.3 |
| 1975.6 | 1483.8 | 1725.75 | -1.6 | 1447.75 | 62.2 | 91 |
| 289.65 | 27.7 | -21.5 | -1.9 | -86.4 | 3.7 | 131 |
| -410.45 | 173.2 | 93.6 | 0.1 | -32.9 | 3.7 | 76 |
| -130.6 | -93.8 | 197.75 | -1.9 | -224.9 | 2.7 | 161.5 |
| 721.45 | 2191.05 | -73.25 | -2.1 | 468.6 | 7.7 | 111 |
| 2182.8 | 10570.05 | 294.6 | -2.1 | 8510.35 | 7.2 | 62.5 |
| 441.3 | -100.1 | -57.9 | -7.4 | -267.25 | 5.2 | 165 |
| 247.55 | 116.3 | -41.25 | -2.1 | -174.1 | -0.8 | 117.8 |
| 297.05 | 50.8 | -93 | -1.1 | -300.9 | 14.2 | 70 |
| 243.2 | -27.2 | -124.65 | 2.4 | -29.25 | 17.7 | 63.3 |
| 65.3 | -141.2 | -120 | 0.9 | -434.05 | 18.2 | 98.5 |
| 790.3 | -30.6 | 239.6 | -2.1 | -13.5 | 1.2 | 60 |
| 116.55 | -55.2 | -78.05 | -2.6 | -341.4 | 5.9 | 68.8 |
| 60.95 | -121.85 | 18.25 | -2.6 | 84.5 | 18.7 | 47 |
| 87.8 | -34.95 | -66.15 | -3.9 | -102.4 | -0.6 | -1.5 |
| 379.05 | 221.3 | -87.55 | -4.6 | -387.4 | 0.2 | 406.5 |
| 548.05 | -144.05 | -103.15 | -9.1 | -278 | -3.8 | 109 |
| 212.4 | -36.05 | -79.3 | -3.6 | -220.25 | 4.7 | 84.3 |
| 428.3 | -118.1 | -1.5 | -2.6 | -162.75 | 13.2 | 183.5 |
| -478.55 | 20.7 | -107.55 | -2.1 | -357.65 | 3.9 | 39 |
| 319.9 | 20.05 | -85.05 | 0.4 | -184.9 | 114.9 | 54.3 |
| 116.8 | 4668.3 | 482 | -1.6 | 4561.5 | 21.2 | 166.5 |
| 40.05 | 1618.7 | 135.9 | -1.9 | 1282.25 | -1.1 | 66 |
| 262.4 | -68.55 | -76.55 | 0.4 | -107.15 | -1.8 | 50.5 |
| 285.55 | 146.95 | 62.6 | -1.1 | 48.85 | 3.2 | 69.8 |
| 410.05 | 2038.2 | -98.9 | -6.6 | -335 | 33.7 | 60 |
| 157.8 | 142.2 | -46 | -5.6 | -282.3 | 31.2 | 68.5 |
| Ave 348.7425394 | 820.3543555 | 21.14252867 | -2.293333333 | 433.9593489 | 19.16333333 | 97.54666667 |
| Stdev 674.0616397 | 3114.576871 | 247.4157409 | 2.483869802 | 2662.75841 | 34.71871684 | 71.64155379 |
| RSD 193.283458 | 379.66238 | 1170.227766 | -108.3082763 | 613.5962774 | 181.1726396 | 73.44336433 |

LUNG CANCER

| EGF (11) FI - Bkgd | IL-5 (10) FI - Bkgd | IL-4 (9) FI - Bkgd | IL-1alpha (32) FI - Bkgd | IL-7 (13) FI - Bkgd | IL-6 (12) FI - Bkgd | GM-CSF (39) FI - Bkgd | IL-17 (30) FI - Bkgd | IL-15 (28) FI - Bkgd | TNF-alpha (40) FI - Bkgd |
|---|---|---|---|---|---|---|---|---|---|
| 8895.5 | -1288 | -517.5 | -3064.5 | -2065 | -961.3 | -296 | 68 | -44.3 | 16.3 |
| 17019 | -1537 | -527.5 | -3208 | -2106.3 | 313.8 | -409 | 992 | -110.5 | 103 |
| 23006 | 229.3 | 3485.8 | 11942.5 | 1072.8 | 7980.3 | -207.3 | 14.8 | -54.5 | 430.5 |
| 13588.3 | -1082.5 | -527 | -3294 | -2134.5 | 251.3 | -547 | -70 | -66 | 137 |
| 18051.5 | -1589 | -482.3 | -3144 | -1856.3 | -1195.8 | -446.5 | -134.3 | -28.3 | -478.3 |
| 25274.3 | -1525.3 | -496 | -2578.3 | -2376.3 | 1799.5 | -493.5 | -65.3 | 57.8 | 1772 |
| 9750 | -1181.3 | 355 | 981 | -2292.8 | -398.5 | -548 | -173 | 42.5 | -418.8 |
| 2608.5 | -1518 | -480.5 | 18611.5 | -1840 | 9565.5 | 2912.5 | 1019.8 | 51.8 | 39 |
| 10102.3 | -1565 | -489.5 | -3266.5 | -2122 | -1301 | -656.5 | -272.3 | -135.8 | -656 |
| 21808.8 | -1529 | 1314 | -3208.5 | -2188.3 | -864.3 | -409.5 | -89.3 | -71.5 | 186.8 |
| 11879.5 | -1522.5 | -350.3 | -3132 | -2206 | -1098.3 | -494.8 | -209.8 | -49 | -362.5 |
| 11066.3 | 1746.8 | 2609.5 | 14619 | -2191.8 | 1751.5 | -684.8 | -95.8 | -116.8 | 725.5 |
| 18963.8 | -1599.3 | -497.8 | -2931.3 | -1267.5 | 328.5 | -371.8 | 220 | -41 | 468.3 |
| 9967.3 | -923 | 1148 | -2087.5 | -2345 | 366.5 | 125.5 | -238.8 | -154.8 | -258 |
| 24419.3 | -1544.8 | 7162.3 | -2284 | -1176.8 | 6370.3 | 1260.8 | 3700.5 | 3.8 | 427 |
| 1139.3 | -1389.3 | -424 | -1998.5 | -2334.8 | -543.8 | -408.8 | -183.8 | 55.8 | -198.3 |
| 7296.5 | -77 | 2183.5 | 8674 | 501.5 | 2033.5 | -665 | -79.3 | 26.8 | 426 |
| 23750.3 | -1295.5 | -528 | -3163.5 | -2096.5 | -1113.5 | -505 | -261.8 | -140.8 | -248.8 |
| 4250.5 | -1547.3 | -312.3 | -3179 | -2411.3 | 98 | -687.5 | -279.3 | -87 | -172.8 |
| 777.8 | -858.8 | -375.5 | -2160.5 | -2411.3 | -746.5 | -568.3 | 559.3 | 128.3 | 1104.5 |
| 1244.8 | -984.8 | -193.8 | -1262.5 | -2138.3 | 798.5 | -417 | 644.5 | -43.3 | 365.3 |
| -3.8 | 527.5 | 108.3 | -1370.3 | -1987.5 | 627.8 | -518.5 | 666.3 | -35.3 | 857.8 |
| 29 | -1295.5 | -297 | -3212.5 | -2262.3 | -1085.8 | -333.5 | -168.8 | 91.3 | -37.5 |
| 23994.3 | -1369 | -375.5 | -3163.5 | -549.5 | 10814.3 | -333.8 | -199.5 | 320.8 | 363.5 |
| 157 | -941 | -193.8 | 2137.8 | -1517.3 | 3532.3 | -535 | 1650.3 | 270.5 | 1220.3 |
| 2147.8 | -1112.5 | -526.5 | -3122.5 | -2143.3 | -776.8 | -458.5 | -37.8 | -58.3 | 1044.8 |
| 25014 | -952.5 | 28.3 | 396.5 | -2081.8 | 996.3 | 1594.5 | 1033 | 408.8 | 1131.8 |
| 7286.8 | -1533.3 | -521.5 | -3288.3 | -1807.5 | 4419.8 | -151.3 | -169 | -11.8 | 1841.8 |
| 25027.3 | 1090.5 | 1402.5 | 8734.3 | -271.3 | 3426.8 | -168 | 63.8 | 202.3 | 694 |
| 25629.3 | -82.5 | 825 | 4169.8 | -1084 | 2058.8 | -232.8 | 65.8 | 177.5 | 851.8 |

LUNG CANCER

| EGF (11) Fl - Bkgd | IL-5 (10) Fl - Bkgd | IL-4 (9) Fl - Bkgd | IL-1alpha (32) Fl - Bkgd | IL-7 (13) Fl - Bkgd | IL-6 (12) Fl - Bkgd | GM-CSF (39) Fl - Bkgd | IL-17 (30) Fl - Bkgd | IL-15 (28) Fl - Bkgd | TNF-alpha (40) Fl - Bkgd |
|---|---|---|---|---|---|---|---|---|---|
| 2410.5 | -440.1 | -521.9 | -2797.4 | -937 | -1083.8 | 1451.3 | -15.1 | -100.3 | -327.6 |
| 3984.8 | 379.4 | -611.6 | -2836.9 | -901.5 | -887.8 | 1157.8 | 200.4 | -72.3 | 280.1 |
| 2955.8 | 165.1 | -94.4 | -2247.4 | -910 | -571 | 1457.8 | 126.1 | -63.8 | 214.6 |
| 2710.8 | -551.1 | -455.1 | -3050.9 | -932 | -1023.5 | 766.8 | 7.9 | -104 | -262.1 |
| 1598.3 | -556.4 | -549.4 | -2933.6 | -926.8 | -1097 | 1102.8 | -23.6 | -135.3 | -444.1 |
| 3324 | -582.1 | -519.4 | -2948.6 | -948 | -1031.8 | 851.8 | -11.4 | -143.8 | -471.6 |
| 1651.8 | -560.6 | -367.9 | -2817.1 | -939.5 | -1047 | 931.3 | 2.1 | -116.8 | -424.9 |
| 141.8 | -575.6 | -598.4 | -2903.6 | -938.5 | -1080.5 | 846.3 | 5.9 | -112 | -431.1 |
| 3016.3 | -552.9 | -537.4 | -2893.6 | -911 | -1057.5 | 1019.3 | 2.9 | -78.3 | -408.6 |
| 3862.3 | -562.4 | -187.6 | -2861.1 | -861 | -1081 | 1083.8 | -27.9 | -109.3 | -378.4 |
| 2380 | -575.4 | -103.4 | -2850.4 | -943.3 | -1067 | 189.8 | -43.1 | -107 | -439.1 |
| 794 | -548.1 | -555.4 | -2862.4 | -940.5 | -1054 | 596.8 | -16.1 | -132.5 | -304.1 |
| 698.5 | -538.6 | -430.4 | -2876.1 | -934 | -1066 | 687.3 | -10.6 | -105 | -246.4 |
| 529 | -574.6 | -127.6 | -2790.1 | -938 | -1089 | 988.3 | -39.1 | -132.8 | -475.1 |
| 1811.8 | -561.1 | -366.1 | -2906.4 | -939.5 | -1094.3 | 945.8 | 0.9 | -106.8 | -478.1 |
| 3392.3 | -579.4 | -333.1 | -2870.1 | -940 | -1009.3 | 1000.3 | -25.4 | -117.8 | -374.9 |
| 1578.3 | -534.9 | -440.6 | -2491.6 | 985.8 | -952.5 | 525.3 | -24.6 | -139 | -334.4 |
| 5477.8 | -568.4 | -535.4 | -2934.4 | -938.5 | -1068 | 775.3 | -31.1 | -126.8 | -408.9 |
| 3161.3 | -541.1 | -517.6 | -2908.6 | -885.3 | -1032 | 674.8 | 50.9 | -69 | -330.9 |
| 1048.8 | -451.6 | -303.6 | -1565.9 | -922.5 | -715.5 | -152.5 | -26.6 | -126.3 | -336.6 |
| 1193.3 | -555.1 | -595.4 | -2981.1 | -934.5 | -1048.3 | 862.3 | 6.4 | -138.5 | -429.9 |
| 2349 | -567.6 | -544.6 | -2766.1 | -939 | -1082.5 | 472 | -22.6 | -149.3 | -489.1 |
| 3698.3 | -584.4 | -406.9 | -2878.4 | -942.3 | -1106.5 | 1052.8 | -22.4 | -127.5 | -478.9 |
| 1603.8 | -566.1 | -586.9 | -2855.1 | -929.5 | -1089 | 868.8 | -31.6 | -126 | -480.9 |
| 1757.8 | -557.1 | -518.6 | -2506.6 | -933.5 | -1009.8 | 805.5 | -60.1 | -124.5 | -517.1 |
| 1618 | -564.9 | -542.4 | -2903.4 | -951.5 | -1096.5 | 1076.8 | -51.1 | -147.8 | -272.1 |
| 3094.3 | -565.1 | -622.6 | -2948.4 | -947.5 | -1111 | 298.8 | -38.6 | -164.5 | -490.9 |
| 413.3 | -528.1 | -629.9 | -3007.6 | -938 | -1026 | 916.8 | -30.1 | -137.5 | -357.1 |
| 4120.3 | -468.1 | -412.9 | -2711.1 | -934.5 | -981.5 | 1017.3 | -27.1 | -112.8 | -336.1 |
| 4175.8 | -513.4 | -425.4 | -2728.1 | -941 | -1015.8 | 1031.8 | -42.9 | -133.5 | -346.1 |

LUNG CANCER

| sE-Selectin (2) | EGF (11) | Leptin (31) | IL-5 (10) | PAI-1 (total) (84) | Resistin (61) | CRP (48) |
|---|---|---|---|---|---|---|
| Fl - Bkgd | Fl - Bkgd | Fl - Bkgd | Fl - Bkgd | Fl - Bkgd | Fl - Bkgd | Fl - Bkgd |
| -3671.9 | 5653 | -6957.4 | -864.05 | 4660.3 | 2971 | 24240.3 |
| -3717.6 | 10501.9 | -7662.4 | -578.8 | 2996.8 | 2213.5 | 4047.5 |
| -3665.9 | 12980.9 | 74.6 | 197.2 | 3443.8 | 1266 | 17317.5 |
| -3637.1 | 8149.55 | -7778.2 | -816.8 | 3143.3 | 1785.3 | 20054.5 |
| -3729.1 | 9824.9 | 699.6 | -1072.7 | 4892 | 3837.8 | 18466.3 |
| -3738.9 | 14299.15 | -7743.4 | -1053.7 | 2623.5 | 1732.3 | 17850 |
| -3735.6 | 5700.9 | -2755.7 | -870.95 | 3432 | 1914.8 | 16446.5 |
| -3731.4 | 1375.3 | -6821.4 | -1046.8 | 3634 | 1933.5 | 17208 |
| -3720.6 | 6559.3 | 13326.8 | -1058.95 | 3842.5 | 2541 | 23049 |
| -3694.6 | 12835.55 | 3898.6 | -1045.7 | 1189.8 | 972.8 | 28118 |
| -3676.6 | 7129.75 | -7761.7 | -1048.95 | 3514.5 | 1533.5 | 7978.3 |
| -3693.9 | 5930.15 | -2428.2 | 599.35 | 3186 | 3589.5 | 8038.5 |
| -3693.4 | 9831.15 | -6222.9 | -1068.95 | 3284.5 | 2880.5 | 8226.3 |
| -3687.4 | 5248.15 | 1035.6 | -748.8 | 1686.5 | 1435 | 16093 |
| -3727.1 | 13115.55 | 14237.1 | -1052.95 | 3552.3 | 1302 | 28147.8 |
| -3733.1 | 2265.8 | -5599.9 | -984.35 | 2676.8 | 429.3 | 27292 |
| -3728.1 | 4437.4 | -7676.7 | -305.95 | 5738 | 3473 | 24705 |
| -3720.9 | 14614.05 | 10298.3 | -1026.6 | 5161.8 | 1755 | 22594 |
| -3729.6 | 3705.9 | -4131.2 | -1044.2 | 4617.3 | 1823.3 | 20327.8 |
| -3726.6 | 913.3 | 3321.1 | -655.2 | 5263 | 1584 | 24366.5 |
| -3708.6 | 1219.05 | -3633.2 | -769.95 | 5488 | 3373.8 | 24571.3 |
| -3734.1 | 1172.6 | 13714.6 | -20.05 | 3665 | 1246.8 | 23394.3 |
| -3722.1 | 1863.65 | 14613.1 | -939.95 | 4597.3 | 1934 | 23957.5 |
| -3720.4 | 12799.05 | -6641.9 | -967.55 | 5006.3 | 1683.5 | 27202.5 |
| -3689.6 | 957.4 | 15484.1 | -749.05 | 4658.8 | 2589 | 27034.8 |
| -3672.4 | 1882.9 | -6923.4 | -838.7 | 2945 | 1321.5 | 27967.5 |
| -3723.1 | 14054.15 | 16599.6 | -758.8 | 2975.5 | 2550 | 17866 |
| -3716.1 | 3850.05 | -5781.4 | -1030.7 | 4780.5 | 2380.3 | 25079 |
| -3739.9 | 14573.8 | -4896.9 | 311.2 | 3194.5 | 1301.5 | 26494.8 |
| -3737.1 | 14902.55 | -5165.7 | -297.95 | 3456 | 3191.3 | 26181 |
| Ave -3710.76 | 6849.641184 | 24.05 | -673.2088352 | 3776.8533333 | 2084.826667 | 20810.51667 |
| Stdev 26.26907977 | 8133.197089 | 8538.619147 | 677.9330761 | 1098.081903 | 853.2641188 | 6683.212178 |
| RSD -0.707916431 | 118.739024 | 35503.61392 | -100.7017497 | 29.07398849 | 40.92734099 | 32.11459035 |

FIG. 6A

LUNG CANCER

| MMP-9 (47) | IL-4 (9) | IL-1alpha (32) | SAA (67) | IL-7 (13) | IL-6 (12) | MMP-13 (66) |
|---|---|---|---|---|---|---|
| Fl - Bkgd | Fl - Bkgd | Fl - Bkgd | Fl - Bkgd | Fl - Bkgd | Fl - Bkgd | Fl - Bkgd |
| 28330.4 | -519.7 | -2930.95 | 397.8 | -1501 | -1022.55 | 2.9 |
| 28065.1 | -569.55 | -3022.45 | 799 | -1503.9 | -287 | 3.1 |
| 27029.1 | 1695.7 | 4847.55 | 1732.5 | 81.4 | 3704.65 | -2.4 |
| 28903.9 | -491.05 | -3172.45 | 1096.5 | -1533.25 | -386.1 | -3.9 |
| 26853.6 | -515.85 | -3038.8 | 100.8 | -1391.55 | -1146.4 | -2.4 |
| 26407.1 | -507.7 | -2763.45 | 1340.3 | -1662.15 | 383.85 | -3.4 |
| 26197.1 | -6.45 | -918.05 | 3567 | -1616.15 | -722.75 | -3.9 |
| 27465.9 | -539.45 | 7853.95 | 131 | -1389.25 | 4242.5 | -4.6 |
| 27660.9 | -513.45 | -3080.05 | 223.3 | -1516.5 | -1179.25 | -4.6 |
| 26431.4 | 563.2 | -3034.8 | 24322.3 | -1524.65 | -972.65 | -0.4 |
| 26820.1 | -226.85 | -2991.2 | 192 | -1574.65 | -1082.65 | -1.4 |
| 27767.1 | 1027.05 | 5878.3 | 512 | -1566.15 | 348.75 | -4.4 |
| 26440.4 | -464.1 | -2903.7 | 205.3 | -1100.75 | -368.75 | -2.4 |
| 28041.4 | 510.2 | -2438.8 | 2146.3 | -1641.5 | -361.25 | -0.6 |
| 27420.9 | 3398.1 | -2595.2 | 26750.8 | -1058.15 | 2638 | -3.4 |
| 28854.4 | -378.55 | -2434.3 | 26697.5 | -1637.4 | -776.55 | -4.9 |
| 28034.4 | 871.45 | 3091.2 | 835 | 743.65 | 540.5 | 4.1 |
| 28005.9 | -531.7 | -3048.95 | 189 | -1517.5 | -1090.75 | -1.1 |
| 28078.4 | -414.85 | -3043.8 | 1254.5 | -1648.3 | -467 | 1.6 |
| 29100.1 | -189.45 | -1863.2 | 539.5 | -1666.9 | -731 | -0.9 |
| 27613.9 | -466.1 | -2121.8 | 3332.8 | -1536.4 | -124.9 | 0.6 |
| 25016.4 | -218.15 | -2068.2 | 1438 | -1463.25 | -227.35 | -7.4 |
| 25435.1 | -351.95 | -3045.45 | 25680 | -1602.3 | -1096.15 | 1.1 |
| 26996.9 | -481.2 | -3009.3 | 25606.5 | -739.5 | 4862.65 | -1.9 |
| 28632.4 | -356.2 | -184.4 | 26905 | -1225.4 | 1261.25 | -2.9 |
| 23275.9 | -534.45 | -3012.95 | 27886.8 | -1547.4 | -936.65 | -4.9 |
| 26659.4 | -297.15 | -1275.95 | 4126.8 | -1514.65 | -57.35 | 7.9 |
| 27913.6 | -575.7 | -3147.95 | 3320.5 | -1372.75 | 1696.9 | -4.6 |
| 27190.1 | 494.8 | 3011.6 | 11225.8 | -602.9 | 1222.65 | 8.4 |
| 27455.6 | 199.8 | 720.85 | 8833 | -1012.5 | 521.5 | 3.6 |
| Ave 27269.89667 | -3.84559044 | -1118.362548 | 7712.92 | -1243.288552 | 241.3225408 | -1.103333333 |
| Stdev 1233.409037 | 1183.906193 | 4301.687931 | 10706.72544 | 779.1491297 | 2492.57725 | 3.811641273 |
| RSD 4.522969237 | -30786.07073 | -384.6416297 | 138.8154608 | -62.66840697 | 1032.882068 | -345.4659764 |

FIG. 6B

| LUNG CANCER | | | | | | | |
|---|---|---|---|---|---|---|---|
| CD40 Ligand (18) | sVCAM-1 (16) | HGF (53) | C-Peptide (73) | sICAM-1 (24) | MMP-7 (30) | Adiponectin (51) |
| Fl - Bkgd | Fl - Bkgd | Fl - Bkgd | Fl - Bkgd | Fl - Bkgd | Fl - Bkgd | Fl - Bkgd |
| 86.3 | 2469.6 | 326.4 | 1136.8 | -2126.7 | 392.8 | 25178.5 |
| 555 | 242.9 | 411.7 | 7232.5 | -6517.7 | 376 | 24662.5 |
| 969.3 | 1989.4 | 293.7 | 11597 | 10285.1 | 286 | 25532.3 |
| 1076 | 2378.9 | 1515.7 | 6044 | -3362.9 | 801 | 25098 |
| 889.8 | 865.1 | 110.7 | 1934 | -3671.2 | 291.5 | 25317 |
| 99.8 | 1921.4 | 657.2 | 15589.5 | -3341.2 | 334 | 25390.3 |
| 299.8 | 1597.4 | 308.4 | 11516.3 | -3994.4 | 379.3 | 25498.8 |
| 279.8 | 2316.9 | 446.2 | 20923 | -3475.7 | 334.8 | 25612.8 |
| 278.8 | 1003.4 | 319.2 | 108 | -987.4 | 190 | 24542.3 |
| 762.3 | 1710.9 | 573.2 | 1505.5 | -2238.9 | 945 | 24574.3 |
| 573.5 | 2309.4 | 358.7 | 1828.8 | -1243.7 | 587.8 | 24285.8 |
| 179.3 | 2186.6 | 772.9 | 13589.3 | 971.3 | 239.5 | 25820 |
| 779.3 | 1330.4 | 307.9 | 13862.3 | -5174.2 | 277 | 24585.8 |
| 530.8 | 1686.4 | 462.7 | 1571 | 4947.6 | 649 | 25493.5 |
| 2242.3 | 1182.9 | 420.7 | 9775.3 | -2781.2 | 418 | 25143.8 |
| 362.3 | 1146.6 | 921.9 | 9058.8 | -618.4 | 3859.5 | 24213.3 |
| 656.8 | 403.9 | 678.4 | 10463 | -2848.2 | 448.8 | 24465 |
| 459 | 739.4 | 1283.7 | 827.5 | -4495.7 | 1087 | 24417 |
| 442.3 | 2682.4 | 776.7 | 14324 | -3270.4 | 300.5 | 17811 |
| -20.8 | -676.1 | 769.2 | 4809 | -1880.4 | 408.5 | 24063.8 |
| 550.8 | 95.1 | 1023.2 | 14290 | -2022.7 | 226 | 25101.3 |
| -117.8 | 731.6 | 1111.9 | 22517.5 | -5094.7 | 304.5 | 23773.3 |
| 639.3 | 1179.4 | 346.2 | 28071.5 | -3902.7 | 777.5 | 20489.8 |
| 282.3 | 522.4 | 774.7 | 28062.5 | -2476.2 | 648.3 | 23679.3 |
| -118.5 | 1032.9 | 1376.4 | | -3977.7 | 237.5 | 25979 |
| 337.8 | 3797.1 | 190.4 | | -944.9 | 1185.5 | 24896 |
| 912.8 | 1249.9 | 313.2 | | -3919.7 | 187.8 | 23848.5 |
| 1618.8 | 738.6 | 483.7 | | -4293.2 | 749 | 25535.5 |
| 302 | 796.4 | -241.1 | | -6267.7 | 308.5 | 24951.5 |
| 279.8 | 1307.4 | -265.8 | | -5800.2 | 278.3 | 23919 |
| Ave 539.6333333 | 1364.62 | 560.9333333 | 10443.2125 | -2484.133333 | 583.63 | 24462.63333 |
| Stdev 495.1416839 | 912.5943554 | 421.3598702 | 8372.039946 | 3305.655549 | 674.4778175 | 1616.928144 |
| RSD 91.75520734 | 66.87534665 | 75.11176379 | 80.16728517 | -133.0707778 | 115.5659952 | 6.609787761 |

FIG. 6C

LUNG CANCER

| GM-CSF (39) Fl - Bkgd | IL-17 (30) Fl - Bkgd | IL-15 (28) Fl - Bkgd | MMP-12 (62) Fl - Bkgd | TNF-alpha (40) Fl - Bkgd | I-TAC (60) Fl - Bkgd | MIF (41) Fl - Bkgd |
|---|---|---|---|---|---|---|
| 577.65 | 26.45 | -72.3 | 0.3 | -155.65 | -7.2 | 145.9 |
| 374.4 | 596.2 | -91.4 | -1.3 | 191.55 | -3.7 | 84.6 |
| 625.25 | 70.45 | -59.15 | 1 | 322.55 | 3.3 | 183.6 |
| 109.9 | -31.05 | -85 | 1 | -62.55 | 56.6 | 184.1 |
| 328.15 | -78.95 | -81.8 | 4.3 | -461.2 | -5.2 | 59.1 |
| 179.15 | -38.35 | -43 | 2.8 | 650.2 | 11.1 | 279.4 |
| 191.65 | -85.45 | -37.15 | -0.3 | -421.85 | -7.9 | 205.1 |
| 1879.4 | 512.85 | -30.1 | -2.8 | -196.05 | 6.6 | 46.4 |
| 181.4 | -134.7 | -107.05 | -1.5 | -532.3 | -11.7 | 121.9 |
| 337.15 | -58.6 | -90.4 | -1.3 | -95.8 | 28.6 | 187.6 |
| -152.5 | -126.45 | -78 | -2.3 | -400.8 | 2.8 | 80.1 |
| -44 | -55.95 | -124.65 | -1.5 | 210.7 | 16.8 | 88.1 |
| 157.75 | 104.7 | -73 | -3.5 | 110.95 | -9.7 | 109.9 |
| 556.9 | -138.95 | -143.8 | 1 | -366.55 | -13.2 | 75.1 |
| 1103.3 | 1850.7 | -51.5 | 0.3 | -25.55 | 54.8 | 104.6 |
| 295.75 | -104.6 | -31 | -2.8 | -286.6 | -12.4 | 66.1 |
| -69.85 | -51.95 | -56.1 | 3.8 | 45.8 | 10.1 | 55.1 |
| 135.15 | -146.45 | -133.8 | -0.8 | -328.85 | -7.7 | 98.4 |
| -6.35 | -114.2 | -78 | -1 | -251.85 | -15.7 | 105.6 |
| -360.4 | 266.35 | 1 | -1.3 | 383.95 | -19.2 | 64.9 |
| 222.65 | 325.45 | -90.9 | -1.8 | -32.3 | 12.8 | 115.9 |
| -23.25 | 321.85 | -92.3 | 0.8 | 184.35 | -16.2 | 121.1 |
| 359.65 | -95.6 | -18.1 | -0.8 | -258.2 | 27.3 | 67.1 |
| 267.5 | -115.55 | 97.4 | -6 | -58.7 | -5.4 | 48.4 |
| 135.25 | 795.1 | 73 | -3.3 | 351.6 | -23.2 | 5688.9 |
| 309.15 | -44.45 | -103.05 | 1.5 | 386.35 | 67.8 | 136.6 |
| 946.65 | 497.2 | 122.15 | 1.3 | 320.45 | 19.3 | 166.6 |
| 382.75 | -99.55 | -74.65 | -1.8 | 742.35 | 52.3 | 171.6 |
| 424.65 | 18.35 | 44.75 | -3.5 | 178.95 | 12.3 | 559.1 |
| 399.5 | 11.45 | 22 | 0 | 252.85 | 12.8 | 527.1 |
| Ave 360.7105077 | 137.8342974 | -30.99166349 | -0.65 | 22.06902133 | 7.896666667 | 331.6 |
| Stdev 782.7030733 | 588.2033168 | 158.5557166 | 2.248639435 | 606.8410315 | 24.11945106 | 1019.012732 |
| RSD 216.9892633 | 426.7467009 | -511.6076349 | -345.9445285 | 2749.74147 | 305.4383841 | 307.3017889 |

FIG. 6D

|  | sE-Selectin (2) | EGF (11) | Leptin (31) | IL-5 (10) | PAI-1 (total) (84) | Resistin (61) | CRP (48) |
|---|---|---|---|---|---|---|---|
|  | FI - Bkgd | FI - Bkgd | FI - Bkgd | FI - Bkgd | FI - Bkgd | FI - Bkgd | FI - Bkgd |
| Asthma vs. Normal | 7.88732E-95 | 0.002375429 | 0.000190735 | 0.001066928 | 5.99103E-27 | 0.000114573 | 0.439547901 |
| Lung Cancer vs. Normal | 1.30916E-06 | 0.000208417 | 0.000815745 | 0.005581507 | 0.00613596 | 0.019056478 | 2.05327E-06 |
| Lung Cancer vs. Asthma | 1.3213E-96 | 4.1423E-07 | 2.65258E-10 | 6.28497E-06 | 1.74477E-25 | 0.001589304 | 8.70444E-05 |

FIG. 7A

|  | MMP-9 (47) | IL-4 (9) | IL-1alpha (32) | SAA (67) | IL-7 (13) | IL-6 (12) | MMP-13 (66) |
|---|---|---|---|---|---|---|---|
|  | FI - Bkgd | FI - Bkgd | FI - Bkgd | FI - Bkgd | FI - Bkgd | FI - Bkgd | FI - Bkgd |
| Asthma vs. Normal | 0.932821151 | 0.996560847 | 0.699314669 | 0.812235674 | 0.931950604 | 0.382911264 | 0.015699864 |
| Lung Cancer vs. Normal | 1.49139E-05 | 0.000208353 | 0.002189059 | 0.004751941 | 0.05496241 | 0.076195528 | 0.305018823 |
| Lung Cancer vs. Asthma | 3.55102E-05 | 0.015820002 | 0.005341776 | 0.003182795 | 0.026613534 | 0.013418408 | 2.69406E-05 |

FIG. 7B

| | CD40 Ligand (18) Fl - Bkgd | sVCAM-1 (16) Fl - Bkgd | HGF (53) Fl - Bkgd | C-Peptide (73) Fl - Bkgd | sICAM-1 (24) Fl - Bkgd | MMP-7 (30) Fl - Bkgd | Adiponectin (51) Fl - Bkgd |
|---|---|---|---|---|---|---|---|
| Asthma vs. Normal | 1.94004E-07 | 2.87131E-20 | 0.029706828 | 5.51622E-09 | 2.46185E-21 | 0.013600064 | 2.78271E-06 |
| Lung Cancer vs. Normal | 0.000250057 | 0.08869949 | 0.411930067 | 0.460053678 | 0.148631587 | 0.031054056 | 0.867711474 |
| Lung Cancer vs. Asthma | 0.198163561 | 1.1163E-14 | 0.004199592 | 4.79234E-07 | 1.21857E-13 | 0.133992639 | 8.3471E-06 |

FIG. 7C

| | GM-CSF (39) Fl - Bkgd | IL-17 (30) Fl - Bkgd | IL-15 (28) Fl - Bkgd | MMP-12 (62) Fl - Bkgd | TNF-alpha (40) Fl - Bkgd | I-TAC (60) Fl - Bkgd | MIF (41) Fl - Bkgd |
|---|---|---|---|---|---|---|---|
| Asthma vs. Normal | 0.014857429 | 0.66172291 | 0.936321205 | 0.066636661 | 0.723224276 | 0.817605393 | 0.024063283 |
| Lung Cancer vs. Normal | 0.710933218 | 0.0815517873 | 0.086324372 | 0.009405627 | 0.229576252 | 0.149755489 | 0.214531395 |
| Lung Cancer vs. Asthma | 0.002379277 | 0.0204077775 | 0.00126166 | 0.759545409 | 0.011931932 | 0.013838225 | 0.334529165 |

FIG. 7D

METHOD OF IDENTIFYING BIOMARKERS IN HUMAN SERUM INDICATIVE OF PATHOLOGIES OF HUMAN LUNG TISSUES

This is an original non-provisional application claiming benefit of U.S. Provisional Application 60/971,440 filed on Sep. 11, 2007, which is incorporated herein by reference.

BACKGROUND OF THE INVENTION

1. Field of the Invention

The present invention relates generally to the diagnosis of pathologies of human lung tissues. More specifically, the present invention relates to the diagnosis of non-small cell lung cancers and asthma by measuring and quantifying expression levels of certain specific biomarkers present in human serum. More specifically, the present invention relates to the identification of biomarkers present in human serum, which, when altered in terms of expression levels from those found in a normal population, are indicative of pathologies associated with human lung tissues and the human respiratory system. By identifying the biomarkers associated with such pathologies, quantifying the expression levels of those biomarkers, and comparing the expression levels with those levels generally expected to present in a normal person's serum, it is possible to detect the presence of the pathologies early on in their progression through simple blood tests and to differentiate among the pathologies.

2. Description of the Related Art

Pathologies of the respiratory system, such as asthma and lung cancer, affect millions of Americans. In fact, the American Lung Association reports that almost 20 million Americans suffer from asthma. The American Cancer Society estimated 229,400 new cancer cases of the respiratory system and 164,840 deaths from cancers of the respiratory system in 2007 alone. While the five year survival rate of cancer cases when the cancer is detected while still localized is 46%, the five year survival rate of lung cancer patients is only 13%. Correspondingly, only 16% of lung cancers are discovered before the disease has spread. Lung cancers are generally categorized as two main types based on the pathology of the cancer cells. Each type is named for the types of cells that were transformed to become cancerous. Small cell lung cancers are derived from small cells in the human lung tissues, whereas non-small-cell lung cancers generally encompass all lung cancers that are not small-cell type. Non-small cell lung cancers are grouped together because the treatment is generally the same for all non-small-cell types. Together, non-small-cell lung cancers, or NSCLCs, make up about 75% of all lung cancers.

A major factor in the diminishing survival rate of lung cancer patients is the fact that lung cancer is difficult to diagnose early. Current methods of diagnosing lung cancer or identifying its existence in a human are restricted to taking X-rays, CT scans and similar tests of the lungs to physically determine the presence or absence of a tumor. Therefore, the diagnosis of lung cancer is often made only in response to symptoms which have presented for a significant period of time, and after the disease has been present in the human long enough to produce a physically detectable mass.

Similarly, current methods of detecting asthma are typically performed long after the presentation of symptoms such as recurrent wheezing, coughing, and chest tightness. Current methods of detecting asthma are typically restricted to lung function tests such as spirometry tests or challenge tests. Moreover, these tests are often ordered by the physician to be performed along with a multitude of other tests to rule out other pathologies or diseases such as chronic obstructive pulmonary disease (COPD), bronchitis, pneumonia, and congestive heart failure.

There does not exist in the prior art a simple, reliable method of diagnosing pathologies of human lung tissues early in their development. Furthermore, there is not a blood test available today which is capable of indicating the presence of a particular lung tissue pathology. It is therefore desirable to develop a method to determine the existence of lung cancers early in the disease progression. It is likewise desirable to develop a method to diagnose asthma and non-small cell lung cancer and to differentiate them from each other and from other lung diseases such as infections at the earliest appearance of symptoms. It is further desirable to identify specific biomarkers present in human blood which, when altered in terms of expression levels, are indicative of the presence of non-small cell lung cancers and/or asthma.

BRIEF SUMMARY OF THE INVENTION

The present invention provides a novel method of detecting and diagnosing non-small cell lung cancers and asthma by performing panel tests of serum obtained from blood samples to determine the expression levels of biomarkers wherein abnormal or altered expression levels is indicative of non-small cell lung cancers and/or asthma. Identification of biomarkers indicative of non-small cell lung cancers and/or asthma was made by comparing the measured expression levels of fifty-nine selected biomarkers in the sera of patients from populations known to have those respective pathologies to a population known not to have the pathologies as confirmed by a physician.

Specifically, human sera were obtained from a "normal population." "Normal population," as used herein is meant to define those individuals known not to have asthma or lung cancers. Fifty-nine biomarkers were selected to be tested. Selection of the biomarkers was chosen from general categories. Cytokines known to be present in immune response, especially in immune response to diseases of the respiratory system were selected. These cytokines are known to be active in antigen-antibody binding in human immune response and in the inflammatory cellular responses observed in both asthma and lung cancer patients. Growth factors known to be present during cell differentiation and proliferation were selected. Biomarkers were selected which are generally known to be active and present in the blood and in metastatic cancers. Generally, these biomarkers are categorized as "metastasis related molecules." Furthermore, biomarkers such as chemokines, cancer antigens, apoptosis related proteins, proteases, adhesion molecules, cell signaling molecules and hormones were also selected to be tested.

After obtaining the sera of the normal population, each serum specimen was divided into aliquots and subjected to a multiplexed immunoassay using automated bead-based technologies publicly available, namely, Luminex's xMAP technology. The Luminex system places specific beads called microspheres in wells on a ninety-six well microplate. Each microsphere is dyed with red and infrared fluorophores at a range of independently varied concentrations of dye, thereby creating unique absorbance signatures for each set of microspheres. This absorbance signature is commonly known as the "address" of the microsphere bead. Each of the microspheres is derivatized with antibodies having binding affinity for a particular type of molecular species, the "antigen." The patient sample is applied to a set of microspheres having different addresses, each carrying antibodies specific for a particular antigen. The antibodies on the beads then bind to the antigens present in the patient sample. In the particular assay method used for the present determinations, a secondary antibody is then applied, followed by a streptavidin conjugated fluorophore that acts as a "reporter."

The beads, with their bound antigen and reporter are then sampled by an instrument. A detection chamber is used to detect the unique absorbance signatures and reporter fluorescence intensity, thereby identifying to which set of analytes each microsphere belongs, thus identifying each specific antibody, antigen or biomarker tested, and producing a quantitative fluorescent signal from the reporter. The fluorescence intensity of the observed signal is proportional to the quantity of antigen bound to the antibodies on the particular bead. Thus, it is possible to calculate the quantity of a particular biomarker in a sample.

The biomarker expression levels determined in the multiplexed immunoassay were recorded for each of the fifty-nine biomarkers for each human serum specimen tested within the sera of the normal patient population. Average expression levels, standard deviation, and relative standard deviation were calculated for the normal population for each biomarker to determine a range of expression levels associated with the normal population.

Next, human sera were obtained for an "asthma population." "Asthma population," as used herein, is meant to define those individuals which were known to have asthma and diagnosed as such by a physician. The expression levels of the same fifty-nine biomarkers that were measured in the normal population were measured in the asthma population using the multiplexed immunoassay. The expression levels resulting from the multiplexed immunoassay were recorded for each of the fifty-nine biomarkers for each human serum specimen tested within the asthma population. Average expression levels, standard deviation, and relative standard deviation were calculated for the asthma population for each biomarker to determine a range of expression levels associated with the asthma population.

Next, human sera were obtained for a "lung cancer population." "Lung cancer population," as used herein, is meant to define those individuals which were known to have non-small cell lung cancers and diagnosed as such by a physician. The same fifty-nine biomarkers that were measured in the normal population and the asthma population were measured in the lung cancer population using the multiplexed immunoassay. The expression levels resulting from the multiplexed immunoassay were recorded for each of the fifty-nine biomarkers for each human serum specimen tested within the lung cancer population. Average expression levels, standard deviation, and relative standard deviation were calculated for the lung cancer population for each biomarker to determine a range of expression levels associated with the lung cancer population.

Next, statistical differences between the normal population, asthma population and lung cancer population were determined for each biomarker tested to identify significant variances between the populations. Student's t statistic was calculated for differences between each population for each biomarker tested. Student's t statistic calculations were performed between the normal population and the asthma population for each biomarker tested. Likewise, Student's t statistic calculations were performed between the normal population and the lung cancer population for each biomarker tested. Finally, Student's t statistic calculations were performed between the lung cancer population and the asthma population. Significance of the statistical differences or variance was determined to be any Student's t value smaller than 0.05, which is the generally accepted scientific standard for significant difference using Student's t statistic calculations.

As a result of the Student's t statistic calculations, twenty-eight biomarkers were identified as having significantly altered expression levels in asthma and/or lung cancer populations when compared to the normal population, and likewise between the asthma and lung cancer populations.

Finally, the biomarkers were organized into subgroups by using nearest neighbor cluster analysis with squared Euclidean distance to determine identifiable sub-groups of patients within the pathologic groups for biomarkers with associated expression levels indicative of asthma and/or lung cancer. Further analysis is ongoing using the nearest neighbor cluster analysis with squared Euclidean distance to determine whether clusters of multiple biomarkers, when examined together, may be indicative of the pathologies of asthma and/or lung cancer.

BRIEF DESCRIPTION OF THE DRAWINGS

FIG. 1A discloses a table showing the first recorded expression levels of the cytokine biomarkers tested from the asthma population;

FIG. 1B discloses a table showing the second recorded expression levels of the cytokine biomarkers tested from the asthma population from each specimen tested and recorded in FIG. 1A;

FIG. 2A through FIG. 2D disclose tables showing the recorded expression levels of the biomarkers for the asthma population, and average, standard deviation, and relative standard deviation calculations each biomarker for the asthma population;

FIG. 3A discloses a table showing the first recorded expression levels of the cytokine biomarkers tested from the normal population;

FIG. 3B discloses a table showing the second recorded expression levels of the cytokine biomarkers tested from the normal population for each specimen tested and recorded in FIG. 3A;

FIG. 4A through FIG. 4D disclose tables showing the recorded expression levels of the biomarkers for the normal population and the average, standard deviation and relative standard deviation calculations each biomarker for the normal population;

FIG. 5A discloses a table showing the first recorded expression levels of they cytokine biomarkers tested from the lung cancer population;

FIG. 5B discloses a table showing the second recorded expression levels of the cytokine biomarkers tested from the lung cancer population for each specimen tested and recorded in FIG. 5A;

FIG. 6A through FIG. 6D disclose tables showing the recorded expression levels of the biomarkers for the lung cancer population and the average, standard deviation and relative standard deviation calculations for each biomarker for the lung cancer population; and FIG. 7A through 7D disclose tables showing the Student's t values between the asthma population, normal population, and lung cancer population for each biomarker tested.

DETAILED DESCRIPTION OF THE INVENTION

The present invention provides a method of identifying biomarkers existing in human blood which indicate the presence of non-small cell lung cancers or asthma when those biomarker's expression levels are altered in comparison with a range of expression levels which are considered normal in individuals not having non-small cell lung cancers or asthma. By determining not only the identity of those biomarkers with altered expression levels associated with the pathologies of non-small cell lung cancers or asthma, but also ranges of expression levels associated within normal populations as well as within populations of those individuals having the specific pathology of asthma or non-small cell lung cancer, it is possible to identify the presence of the pathology in a patient through a blood test much earlier in the progression of the disease.

Human blood samples were collected from volunteers. Thirty samples were collected from individuals known not to have either non-small cell lung cancer or asthma. These thirty samples comprise, and are referred to herein as, the "normal population." Twenty-eight blood samples were collected from individuals known to have asthma and diagnosed as such by a physician. These twenty-eight samples comprise, and are referred to herein as, the "asthma population." Thirty blood samples were collected from individuals known to have non-small cell lung cancers and diagnosed as such by a physician. These thirty samples comprise, and are referred to herein as the "lung cancer population." Finally, seventy-one blood samples were collected from individuals known to have risks of lung cancer due to a history of cigarette smoking as recorded by a physician. These seventy one samples are the subject of ongoing research and experimentation, and are accordingly not discussed herein.

The blood samples were collected from volunteers under an IRB approved protocol, following informed consent using standard venipuncture techniques into sterile 10 ml BD Vacutaine® glass serum red top tubes. The blood samples were then left undisturbed at room temperature for thirty minutes to allow the blood to clot. The samples were spun in a standard benchtop centrifuge at room temperature at two thousand rpm for ten minutes to separate the serum from the blood samples. The serum of each sample was then removed by pipetting the serum into secondary tubes. The secondary tubes were pre-chilled on ice to ensure the integrity of each serum specimen by limiting degradation due to proteolysis and denaturation. The serum specimens from each sample collected were then divided into 1.0 ml aliquots in pre-chilled Cryovial tubes on ice. The aliquots from the serum specimens were stored at a temperature at least as cold as eighty degrees below Celsius (−80° C.). The processing time was no more than one hour from phlebotomy to storing at −80° C.

Research was performed to select biomarkers which it was believed that altered expression levels would be associated with asthma or lung cancer. As used herein, the term "lung cancer" is meant to encompass those lung cancers which are known to be non-small celled lung cancers. The biomarkers selected were identified through research of the scientific literature for reports of molecular species that were known or likely to be modulated in disease states including asthma, lung cancer, chronic obstructive pulmonary disease, infectious disease due to bacterial and viral invasion. Biomarkers were further selected based on their likely involvement in or association with other cancers. In addition, biomarkers were selected with the aid of database searches of electronically stored on-line databases such as that maintained by the National Center for Biotechnology Information and others. As a result of the research efforts, it was believed that certain general categories of biomarkers should be tested. Those categories were cytokines, chemokines, growth and angiogenic factors, metastasis related molecules, cancer antigens, apoptosis related proteins, proteases, adhesion molecules, cell signaling molecules and hormones.

From among these general categories, the following fifty-nine biomarkers were selected to be tested: CD40, Hepatocyte Growth Factor ("HGF"), I-TAC, Leptin, Matrix Metalloproteinase ("MMP") 1, MMP 2, MMP3, MMP 7, MMP 8, MMP 9, MMP 12, MMP 13, CD40 Soluble Ligand ("CD40 Ligand"), Epidermal Growth Factor ("EFG"), Eotaxin, Fractalkine, Granulocyte Colony Stimulating Factor ("G-CSF"), Granulocyte Macrophage Colony Stimulating Factor ("GM-CSF"), Interferon γ ("IFN γ"), Interleukin ("IL") 1α, IL-1β, IL-1ra, IL-2, IL-4, IL-5, IL-6, IL-7, IL-8, IL-10, IL-12(p40), IL-12(p70), IL-13, IL-15, IL-17, IP-10, Monocyte Chemotactic Protein 1 ("MCP-1"), Macrophage Inflammatory Protein ("MIP") 1α, MIP-1β, Transforming Growth Factor α ("TGF α"), Tumor Necrosis Factor α ("TNF α"), Vascular Endothelial Growth Factor ("VEGF"), Insulin, C-peptide, Glucagon Like Protein-1/amyline ("GLP-1/amylin"), Amylin (total), Glucagon, Adiponectin, Plasminogen Activator Inhibitor 1 ("PAI-1") (active/total), Resistin, sFas, sFasL, Macrophage Migration Inhibitory Factor ("MIF"), sE-Selectin, Soluble Vascular Cell Adhesion Molecule ("sVCAM"), Soluble Intracellular Adhesion Molecule ("sICAM"), Myeloperoxidase ("MPO"), C-Reactive Protein ("CRP"), Serum Amyloid A ("SAA"), and Serum Amyloid P ("SAP").

Each serum specimen for each of the normal, asthma and lung cancer populations were screened for each of the fifty-nine biomarkers by subjecting the serum specimens to a quantitative multiplexed immunoassay using automated bead-based technologies. Specifically, Luminex's xMAP technology was used to conduct the immunoassay as previously described hereinabove.

Eight different assay kits were used with the Luminex xMAP technology to screen the biomarkers, namely Millipore's Human Cytokine/Chemokine (Cat# MPXHCYTO-60K, Human Endocrine (Cat# HENDO-65K), Human Serum Adipokines (Cat# HADKI-61K), Human Sepsis/Apoptosis (Cat# HSEP-63K), Human Cardiovascular Panel 1 (Cat# HCVD 1-67AK) and Human Cardiovascular Panel 2 (HCVD2-67BK) along with R&D Systems, Inc.'s Human Fluorokine MAP Profiling Base Kit B (Cat# LUB00) and Human Fluorokine MAP MMP Profiling Base Kit (Cat# LMP000). The expression levels resulting from the multiplexed immunoassay were recorded for each of the fifty-nine biomarkers for each serum specimen for each population. Averages, standard deviations, and relative standard deviations for each biomarker for each population were recorded.

Student's t test was then used to measure inter-pathology differences for each particular biomarker between each population. Comparisons of measurements of each biomarker for the samples from normal patients were compared to those of the samples from patients suffering from lung cancer and also to those measurements from the analysis of samples derived from patients suffering from asthma. In addition, the measurements for the lung cancer patients were compared to the measurements for the asthma patients using the Student's t statistic.

The significance of the differences in biomarker expression levels were used to rank the relative importance of the biomarkers. That is to say, those biomarkers that were found to be most significantly different between pathologies were classed as relatively more important. The measurements of mean fluorescence intensity were examined and data for all biomarkers having intensities that did not depart significantly from the average intensities of specimens in the other populations were excluded from further analysis. Those biomarkers having relatively low relative standard deviation were classed as more significant than those having relatively high standard deviation.

The direction of variation, i.e. whether the average level of a particular marker increased or decreased in any pathology relative to any of the other pathologies was not used to judge the relative significance of a particular marker. In this way, a group of biomarkers was assembled that showed high variability between pathologies (low Student's t value), relatively low relative standard deviation and good instrumental detectability (defined as non-zero uncorrected mean fluorescence intensity). Those calculations were used to test the efficiency of the immunoassay and analyzed to determine the biomarkers which showed significant differences in expression levels between the expression levels of the normal population, as well as to determine reference ranges which are characteristic of and associated with the pathologies of lung cancer and/or asthma. The numerical measurements of mean fluorescence intensity derived from the analysis as reported in FIG. 1A through FIG. 6D are the mean fluorescence intensities as reported by the Luminex xMAP instrument operating software.

FIGS. 1A through 7D show the data recorded, calculated and observed for the twenty-eight biomarkers which were determined to have significant differences in expression levels between asthma, normal and lung cancer populations. Referring to FIG. 1A, FIG. 1B, FIG. 3A, FIG. 3B, FIG. 5A and FIG. 5B, the expression levels for the cytokines EGF, IL-5, IL-4, IL-1α, IL-7, IL-6, GM-CSF, IL-17, IL-15 and TNF α were screened twice for the asthma population, normal population and lung cancer population, respectively. These cytokines were the first sets of biomarkers screened, and thus, were screened twice to verify the validity of multiplexed immunoassay results as well as calibration curves.

FIG. 1A shows the first recorded expression levels for the cytokines in the asthma population. FIG. 1B shows the second recorded expression levels for the cytokines in the asthma population. FIG. 3A shows the first recorded expression levels for the cytokines in the normal population. FIG. 3B shows the second recorded expression levels for the cytokines in the normal population. FIG. 5A shows the first recorded expression levels for the cytokines in the lung cancer population. FIG. 5B shows the second recorded expression levels for the cytokines in the lung cancer population. The data recorded for both screenings of the cytokines for each population were recorded in the same order to ensure comparison of the levels was specific to the same specimen. For instance, the first recorded value in the top horizontal row in FIG. 1A was recorded from the same specimen as shown in the recorded value in the top horizontal row in FIG. 1B, and so forth.

Referring to FIG. 2A through FIG. 2D, the recorded expression levels for twenty-eight biomarkers for the twenty-eight specimens tested in the asthma population are shown. The expression levels for sE-Selectin, EGF, Leptin, IL-5, PAI-1 Resistin, CRP, MMP-9, IL-4, IL 1α, SAA, IL-7, IL-6, MMP13, CD40 Ligand, sVCAM-1, HGF, C-Peptide, sICAM-1, MMP-7, Adiponectin, GM-CSF, IL-17, IL-15, MMP-12, TNF α, I-TAC, and MIF are shown in FIG. 2A through 2D. These biomarkers are the twenty-eight biomarkers which showed significant variance between the asthma, normal and lung cancer populations. The values shown in FIG. 2A through FIG. 2D in the columns for the cytokines EGF, IL-5, IL-4, IL-1 α, IL-7, IL-6, GM-CSF, IL-17, IL-5 and TNF α are the average of the two values for each specimen in those columns recorded in FIG. 1A and FIG. 1B. The rest of the values shown in FIG. 2A through FIG. 2D are the recorded expression levels for the biomarkers for each specimen tested in the asthma population.

Referring to FIG. 4A through FIG. 4D, the recorded expression levels for the twenty-eight biomarkers for the thirty specimens tested in the normal population are shown. As with FIG. 2A through FIG. 2D, the values shown in FIG. 4A through FIG. 4D in the columns for the cytokines EGF, IL-5, IL-4, IL-1 α, IL-7, IL-6, GM-CSF, IL-17, IL-5 and TNF α are the average of the two values for each specimen in those columns recorded in FIG. 3A and FIG. 3B. The rest of the values shown in FIG. 4A through FIG. 4D are the recorded expression levels for the biomarkers for each specimen tested in the normal population.

Referring to FIG. 6A through FIG. 6D, the recorded expression levels for the twenty-eight biomarkers for the thirty specimens tested in the lung cancer population are shown. Thirty specimens were recorded in the lung cancer population for all of the biomarkers tested except for C-peptide, for which only twenty-four of the thirty specimens were recorded. As with FIG. 2A through FIG. 2D and FIG. 4A through FIG. 4D, the values shown in FIG. 6A through FIG. 6D in the columns for the cytokines EGF, IL-5, IL-4, IL-1 α, IL-7, IL-6, GM-CSF, IL-17, IL-5 and TNF α are the average of the two values for each specimen in those columns recorded in FIG. 5A and FIG. 5B. The rest of the values shown in FIG. 6A through FIG. 6D are the recorded expression levels for the biomarkers for each specimen tested in the lung cancer population.

Once the biomarker expression levels were obtained and recorded, and the average, standard deviation and relative standard deviation calculated, further analysis of the statistical differences for each biomarker between the normal, asthma and lung cancer populations was performed. To determine the significance of the variance in expression levels for each biomarker between the populations, Student's t values were calculated using the formula:

$$t = \frac{\overline{X}_1 - \overline{X}_2}{S_{X_1 X_2} \cdot \sqrt{\frac{1}{n_1} + \frac{1}{n_2}}}$$

where $$S_{X_1 X_2} = \sqrt{\frac{(n_1 - 1)S_{X1}^2 + (n_2 - 1)S_{X2}^2}{n_1 + n_2 - 2}}$$

$S_{X_1 X_2}$ is the unbiased estimator of the variance of the two samples. $n_1$ represents the number of participants (number of specimens) in the first group (population) and $n_2$ represents the number of participants (number of specimens) in the second group (population). $n_1 - 1$ is the number of degrees of freedom for the first group or population and $n_2$ is the number of degrees of freedom for the second group. The total sample size minus two (that is, $n_1 + n_2 - 2$) is the total number of degrees of freedom, which is used in significance testing. The statistical significance level associated with the Student's t value calculated in this way is the probability that, under the null hypothesis of equal means, the absolute value of t could be as large as indicated or larger just by chance. In other words, the Student's t statistical calculation is a two-tailed test, testing whether the means are different when, if they are, either one may be the larger.

In calculating the Student's t values, significance of the variance of expression levels between the populations was determined on the criteria that any Student's t value smaller than 0.05 was considered to be a variance significant to indicate the presence of the given pathology, whether asthma or lung cancer. Using a criterion of 0.05 is generally accepted in the scientific community. Any Student's t value larger than 0.1 was considered to be insignificant to indicate the presence of the given pathology. Furthermore, any Student's t value between 0.05 and 0.1 was determined to be insignificant.

However further experimentation and testing could be done for the biomarkers with student's t values of 0.05 to 0.1 between the populations to verify their lack of significance. For instance, as shown in FIG. 7B, comparison of IL-7 between the lung cancer population and the normal population yielded a Student's t value of 0.05496241, which is only slightly greater than the 0.05 threshold. Further experimentation and testing could be done for both the lung cancer population and the normal population to verify whether the Student's t value is significant for the indication of lung cancer.

Referring now to FIG. 7A through FIG. 7D, the Student's t values calculated comparing each biomarker for each population is shown. It should be noted that the Student's t values shown in FIG. 7A through FIG. 7D are calculated on the basis that each of the asthma, normal, and lung cancer populations has a single mean and a normal distribution. It is possible that, in addition to calculating the Student's t values based on a single mean across a population, there are subgroups within each population that could further be analyzed and calculated to show significant variance. For instance, the expression levels for each biomarker for each specimen tested could be broken into low, medium and high subgroups based on each specimen's expression level, and each subgroup compared between the populations within each biomarker.

Still referring to FIG. 7A through FIG. 7D, Student's t values were calculated first to compare the asthma population to the normal population. Significant variance between the asthma population and the normal population was determined from the Student's t calculation for the biomarkers sE-Selectin, EGF, Leptin, IL-5, PAI-1, Resistin, MMP-13, CD40 Ligand sVCAM-1, HGF, C-Peptide, sICAM-1, MMP-7, Adiponectin, GM-CSF and MIF. This determination was made on the basis that, when comparing the twenty-eight specimens from the asthma population with the thirty specimens from the normal population using the Student's t formula described herein, the Student's t value for each of these biomarkers was smaller than 0.05. Variance was determined to be insignificant between the asthma population and the normal population for the biomarkers CRP, MMP-9, IL-4, IL-1α, SAA, IL-7 and IL-6, as the Student's t values for each of these was significantly greater than 0.05.

As also shown in FIG. 7A through 7D, Student's t values were calculated to compare the lung cancer population to the normal population. Significant variance between the lung cancer population and the normal population was determined from the Student's t calculation for the biomarkers sE-Selectin, EGF, Leptin, IL-5, PAI-1, Resistin, CRP, MMP-9, IL-4, IL-1α, SAA, IL-7, CD40 Ligand, MMP-7 and MMP-12. Again, this determination was made on the basis that, when comparing the thirty specimens from the lung cancer population with the thirty specimens from the normal population using the Student's t formula described herein, the Student's t value for each of these biomarkers was smaller than 0.05. Variance was determined to be insignificant between the lung cancer population and the normal population for the biomarkers MMP-13, HGF, C-Peptide, sICAM, Adiponectin, GM-CSF, IL-17, TNF α, ITAC and MIF, as the Student's t values for each of these biomarkers was significantly greater than 0.05.

Three biomarkers had Student's t values only slightly greater than 0.05 between the lung cancer population and the normal population. Specifically, when comparing the lung cancer population to the normal population, IL-6 had a Student's t value of 0.076195528, sVCAM-1 had a Student's t value of 0.08869949, and IL-15 had a Student's T value of 0.086324372. These biomarkers are regarded herein as having insignificant variance between the lung cancer population and the normal population. However, due to the fact that the Student's t values for these three biomarkers are close to 0.05, it is possible that further experimentation, including, but not limited to, further research of subgroups within each population, may determine these biomarkers to be significantly varied between the normal and lung cancer populations.

Finally, as shown in FIG. 7A through FIG. 7D, further analysis was done by calculating the Student's t values to compare the lung cancer population to the asthma population. Significant variance between the lung cancer population and the asthma population was determined from the Student's t calculation for the biomarkers sE-Selectin, EGF, Leptin, IL-5, PAI-1, Resistin, CRP, MMP-9, IL-4, IL-1α, SAA, IL-7, IL-6, MMP-13 sVCAM, HGF, C-Peptide, sICAM, Adiponectin, GM-CSF, IL-17, IL-15, TNF α and I-TAC. This determination was made on the basis that, when comparing the thirty specimens from the lung cancer population with the twenty-eight specimens from the asthma population using the Student's t formula described herein, the Student's t value for each of these biomarkers was smaller than 0.05. Variance was determined to be insignificant between the lung cancer population and the asthma population for the biomarkers CD40 Ligand, MMP-7, MMP-12 and MIF, as the Student's t values for each of these biomarkers was significantly greater than 0.05.

To date, the panel of fifty-nine biomarkers tested and examined, as described herein, is the largest panel of biomarkers to be simultaneously tested and examined for the lung tissue pathologies of asthma and lung cancer. By obtaining the expression levels of these biomarkers from many specimens across the normal population, lung cancer population, and asthma population, and obtaining average expression levels of each population, it is possible to determine characteristic reference ranges of expression levels associated with each population for each biomarker. The significance of the variance of each biomarker compared across each population was verified by calculating Student's t values. With the determination of characteristic reference ranges of expression levels for each biomarker, it is possible to determine the existence of asthma or lung cancer in a patient simply by subjecting the patient's blood to a simple blood test to determine the expression levels, and comparing the results of the expression levels to the characteristic reference ranges to determine the existence of the pathology.

Specifically, to determine the existence of lung cancer or asthma, the biomarkers, sE-Selectin, EGF, Leptin, IL-5, PAI-1, Resistin, CRP, MMP-9, IL-4, IL-1α, SAA, IL-7, IL-6, MMP-13, CD40 Ligand, sVCAM-1, HGF, C-Peptide, sICAM-1, MMP-7, Adiponectin, GM-CSF, IL-1 7, IL-1 5, MMP-12, TNF α, I-TAC, and MIF, can be tested from the patient's blood and compared to the respective characteristic reference ranges, because these biomarkers are found to be indicative of lung cancer or asthma where their respective expression levels vary from the range of expression levels associated with individuals who do not have lung cancer or asthma. Of these twenty-eight biomarkers, where expression levels of sE-Selectin, EGF, Leptin, IL-5, PAI-1, Resistin, MMP-13, CD40 Ligand, sVCAM-1, HGF, C-Peptide, sICAM-1, MMP-7, Adiponectin, GM-CSF and MIF are found to be altered, asthma is indicated. Where expression levels of sE-Selectin, EGF, Leptin, IL-5, PAI-1, Resistin, CRP, MMP-9, IL-4, IL-1α, SAA, IL-7, CD40 Ligand, MMP-7 and MMP-12 are significantly altered, lung cancer is indicated. Thus, determining the existence of lung cancer or asthma in a patient may now be accomplished by blood tests in a way which has never been done before.

In addition to determining the existence of lung cancer or asthma early in the development of the disease, the biomarkers identified herein as indicative of such pathologies could be used and applied in related ways to further the goal of treating lung cancer and/or asthma. For instance, the biomarkers could be assembled in a biomarker panel wherein any or all of the biomarkers are assembled into a single bead based panel or kit for a bead based immunoassay, or other non-bead based assay to diagnose or detect the presence of lung cancer and/or asthma. The biomarkers could also be used and applied to the field of pharmacology to evaluate the response of a patient to therapeutic interventions such as drug treatment, radiation/chemotherapy, or surgical treatment. Furthermore, the biomarkers or a kit comprising a panel of the biomarkers could be used for routine testing of a patient to monitor health status of a patient who is at greater risk of the pathologies, such as smokers, or those with family histories of the pathologies.

Although the invention has been described with reference to specific embodiments, this description is not meant to be construed in a limited sense. Various modifications of the disclosed embodiments, as well as alternative embodiments of the invention will become apparent to persons skilled in the art upon the reference to the description of the invention. It is, therefore, contemplated that the appended claims will cover such modifications that fall within the scope of the invention.

We claim:

1. A method of identifying altered biomarker expression levels in a human serum specimen to diagnose pathologies of human lung tissues comprising:
    obtaining said human serum specimen to be tested for said altered biomarker expression levels;
    selecting biomarkers for measuring said biomarker expression levels in said human serum specimen;
    measuring said biomarker expression levels in said human serum specimen, said measuring step comprising dividing said human serum specimen into aliquots, placing said aliquots of said human serum specimen into a plurality of wells on a microplate, said plurality of wells having antibody derivitized dye coded beads therein to detect the presence of a particular biomarker selected during said selecting step, subjecting said microplate with said aliquots of said human serum specimens to a bead-based multiplexing assay, observing and measuring the resulting said biomarker expression levels from said bead-based multiplexing assay;
    determining substantially unaltered biomarker expression levels for the same biomarkers selected in said selecting step, said unaltered biomarker expression levels being determined from a population of human serum specimens not having said pathologies of human lung tissues;
    comparing said biomarker expression levels of said human serum specimen obtained in said obtaining step to said unaltered biomarker expression levels from said population of human serum specimens;
    determining whether said biomarker expression levels of said human serum specimen are altered;
    wherein said altered biomarker expression levels are indicative of said pathologies of said human lung tissues; and
    wherein said pathologies of said human lung tissues comprise non-small cell lung cancers and asthma.

2. The method of identifying altered biomarker expression levels as recited in claim 1 wherein said biomarkers selected during said selecting step comprise:
    at least one cytokine selected from a group consisting of Epidermal Growth Factor, Interleukin 1α, Interleukin 4, Interleukin 5, Interleukin 6, Interleukin 7, Interleukin 15, Interleukin 17, Granulocyte Macrophage Colony-Stimulating Factor, Tumor Necrosis Factor α, Macrophage Migration Inhibitory Factor, sE-Selectin, Soluble Vascular Cell Adhesion Molecule, Soluble Intracellular Adhesion Molecule.

3. The method of identifying altered biomarker expression levels as recited in claim 1 wherein said biomarkers selected during said selecting step comprise at least one growth factor, said growth factor comprising Hepatocyte Growth Factor.

4. The method of identifying altered biomarker expression levels as recited in claim 1 wherein said biomarkers selected during said selecting step comprise at least one metastasis related molecule selected from a group consisting of C-Reactive Protein, Serum Amyloid A, Matrix Metalloproteinase 7, Matrix Metalloproteinase 9, Matrix Metalloproteinase 12, Matrix Metalloproteinase 13, and CD40 Soluble Ligand.

5. The method of identifying altered biomarker expression levels as recited in claim 1 wherein said biomarkers selected during said selecting step comprise at least one cell signaling molecule selected from a group consisting of Leptin, Plasminogen Activator Inhibitor-1, Resistin, C-Peptide, Adiponectin, and I-TAC.

6. The method of identifying altered biomarker expression levels as recited in claim 2 wherein said biomarkers selected during said selecting step comprise at least one growth factor, said growth factor comprising Hepatocyte Growth Factor.

7. The method of identifying altered biomarker expression levels as recited in claim 2 wherein said biomarkers selected during said selecting step further comprise at least one metastasis related molecule selected from a group consisting of C-Reactive Protein, Serum Amyloid A, Matrix Metalloproteinase 7, Matrix Metalloproteinase 9, Matrix Metalloproteinase 12, Matrix Metalloproteinase 13 and CD40 Soluble Ligand.

8. The method of identifying altered biomarker expression levels as recited in claim 2 wherein said biomarkers selected during said selecting step further comprise at least one cell signaling molecule selected from a group consisting of Leptin, Plasminogen Activator Inhibitor-1, Resistin, C-Peptide, Adiponectin, and I-TAC.

9. The method of identifying altered biomarker expression levels as recited in claim 3 wherein said biomarkers selected during said selecting step further comprise at least one metastasis related molecule selected from a group consisting of C-Reactive Protein, Serum Amyloid A, Matrix Metalloproteinase 7, Matrix Metalloproteinase 9, Matrix Metalloproteinase 12, Matrix Metalloproteinase 13 and CD40 Soluble Ligand.

10. The method of identifying altered biomarker expression levels as recited in claim 3 wherein said biomarkers selected during said selecting step further comprise at least one cell signaling molecule selected from a group consisting of Leptin, Plasminogen Activator Inhibitor-1, Resistin, C-Peptide, Adiponectin, and I-TAC.

11. The method of identifying altered biomarker expression levels as recited in claim 4 wherein said biomarkers selected during said selecting step further comprise at least one cell signaling molecule selected from a group consisting of Leptin, Plasminogen Activator Inhibitor-1, Resistin, C-Peptide, Adiponectin, and I-TAC.

12. The method of identifying altered biomarker expression levels as recited in claim 6 wherein said biomarkers selected during said selecting step further comprise at least one metastasis related molecule selected from a group consisting of C-Reactive Protein, Serum Amyloid A, Matrix Metalloproteinase 7, Matrix Metalloproteinase 9, Matrix Metalloproteinase 12, Matrix Metalloproteinase 13, and CD40 Soluble Ligand.

13. The method of identifying altered biomarker expression levels as recited in claim 6 wherein said biomarkers selected during said selecting step further comprise at least one cell signaling molecule selected from a group consisting of Leptin, Plasminogen Activator Inhibitor-1, Resistin, C-Peptide, Adiponectin, and I-TAC.

14. The method of identifying altered biomarker expression levels as recited in claim 7 wherein said biomarkers selected during said selecting step further comprise at least one cell signaling molecule selected from a group consisting of Leptin, Plasminogen Activator Inhibitor-1, Resistin, C-Peptide, Adiponectin, and I-TAC.

15. The method of identifying altered biomarker expression levels as recited in claim 12 wherein said biomarkers selected during said selecting step further comprise at least one cell signaling molecule selected from a group consisting of Leptin, Plasminogen Activator Inhibitor-1, Resistin, C-Peptide, Adiponectin, and I-TAC.

16. The method of identifying altered biomarker expression levels as recited in claim 15 wherein:
   said at least one cytokine selected during said selecting step is selected from the group consisting of Epidermal Growth Factor, sE-Selectin, Interleukin 5, Granulocyte Macrophage Colony-Stimulating Factor, Soluble Vascular Cell Adhesion Molecule, Soluble Intracellular Adhesion Molecule, and Macrophage Migration Inhibitory Factor;
   said at least one metastasis related molecule selected during said selecting step is selected from the group consisting of Matrix Metalloproteinase 13, CD40 Soluble Ligand and Matrix Metalloproteinase 7;
   said at least one cell signaling molecule selected during said selecting step is selected from the group consisting of C-Peptide, Leptin, Resistin, Plasminogen Activator Inhibitor-I and Adiponectin; and
   said altered expression levels are indicative of the pathology of asthma.

17. The method of identifying altered biomarker expression levels as recited in claim 15 wherein:
   said at least one cytokine selected during said selecting step is selected from the group consisting of Epidermal Growth Factor, sE-Selectin, Interleukin 5, Interleukin 4, Interleukin 1α, and Interleukin 7;
   said at least one metastasis related molecule selected during said selecting step is selected from the group consisting of C-Reactive Protein, Matrix Metalloproteinase 9, Serum Amyloid A, CD40 Soluble Ligand, Matrix Metalloproteinase 7 and Matrix Metalloproteinase 12;
   said at least one cell signaling molecule selected during said selecting step is selected from the group consisting of Plasminogen Activator Inhibitor-1, Resistin, and Leptin; and
   said altered expression levels are indicative of the pathologies of non-small cell lung cancers.

18. A method of identifying biomarkers present in human serum which are indicative of pathologies of human lung tissues when expression levels of said biomarkers are altered in comparison to expression levels of the same said biomarkers in serum from humans not having said pathologies, said method comprising the steps of:
   first obtaining a plurality of human sera from a population of humans without said pathologies of said human lung tissues;
   second obtaining a plurality of human sera from a population of humans with asthma;
   third obtaining a plurality of human sera from a population of humans with non-small cell lung cancers;
   selecting said biomarkers for measuring said expression levels of said biomarkers;
   first measuring said expression levels of said biomarkers from said population of humans without said pathologies of said human lung tissues;
   second measuring said expression levels of said biomarkers from said population of humans with said asthma;
   third measuring said expression levels of said biomarkers from said population of humans with said non-small cell lung cancers;
   first comparing said expression levels of said biomarkers from said population of humans with said asthma to said expression levels of said biomarkers from said population of humans without said pathologies of said human lung tissues;
   second comparing said expression levels of said biomarkers from said population of humans with said non-small cell lung cancers to said expression levels of said biomarkers from said population of humans without said pathologies of said human lung tissues;
   third comparing said expression levels of said biomarkers from said population of humans with said asthma to said expression levels of said biomarkers from said population of humans with said non-small cell lung cancer;
   identifying which of said biomarkers selected during said selecting step are indicative of said pathologies of said human lung tissues; and
   wherein said pathologies comprise said asthma and said non-small cell lung cancers.

19. The method of identifying biomarkers present in human serum which are indicative of pathologies of human lung tissues as recited in claim 18 wherein each of said first measuring step, said second measuring step, and said third measuring step comprises:
   dividing each of said plurality of human sera into aliquots;
   placing said aliquots into a plurality of wells on a microplate, each of said wells having a bead therein to detect the presence of a particular biomarker to be tested;
   subjecting said microplate with said aliquots to a bead-based multiplexing assay; and
   recording the resulting said expression levels of said biomarkers for each said biomarker selected during said selecting step.

20. The method of identifying biomarkers present in human serum which are indicative of pathologies of human lung tissues as recited in claim 19 wherein said biomarkers selected during said selecting step comprise:
   sE-Selectin, Epidermal Growth Factor, Leptin, Interleukin 5, Plasminogen Activator Inhibitor-1, Resistin, C-Reactive Protein, Matrix Metalloproteinase 9, Interleukin 4, Interleukin 1α, Serum Amyloid A, Interleukin 7, Interleukin 6, Matrix Metalloproteinase 13, CD40 Soluble Ligand, Soluble Vascular Cell Adhesion Molecule 1, Hepatocyte Growth Factor, C-Peptide, Soluble Intracellular Adhesion Molecule 1, Matrix Metalloproteinase 7, Adiponectin, Granulocyte Macrophage Colony-Stimulating Factor, Interleukin 17, Interleukin 15, Matrix Metalloproteinase 12, Tumor Necrosis Factor α, I-TAC, and Macrophage Migration Inhibitory Factor.

21. The method of identifying biomarkers present in human serum which are indicative of pathologies of human lung tissues as recited in claim 19 wherein said biomarkers selected during said selecting step comprise:

Epidermal Growth Factor, sE-Selectin, Interleukin 5, Granulocyte Macrophage Colony-Stimulating Factor, Soluble Vascular Cell Adhesion Molecule, s Intracellular Adhesion Molecule, Macrophage Migration Inhibitory Factor, Matrix Metalloproteinase 13, CD40 Soluble Ligand, Matrix Metalloproteinase 7, C-Peptide, Leptin, Resistin, Plasminogen Activator Inhibitor-1, Adiponectin and Hepatocyte Growth Factor; and said altered expression levels are indicative of the pathology of asthma.

22. The method of identifying biomarkers present in human serum which are indicative of pathologies of human lung tissues as recited in claim 19 wherein said biomarkers selected during said selecting step comprise:

Epidermal Growth Factor, sE-Selectin, Interleukin 5, Interleukin 4, Interleukin 1α, Interleukin 7, C-Reactive Protein, Matrix Metalloproteinase 9, Serum Amyloid A, CD40 Soluble Ligand, Matrix Metalloproteinase 7 Matrix Metalloproteinase 12, Plasminogen Activator Inhibitor-1, Resistin, and Leptin; and said altered expression levels are indicative of the pathologies of non-small cell lung cancers.

23. The method of identifying biomarkers present in human serum which are indicative of pathologies of human lung tissues as recited in claim 20 wherein said first comparing step comprises:

first calculating statistical significances of variances for each biomarker selected during said selecting step between said population of humans with said asthma and said population of humans without said pathologies of said human lung tissues, said first calculating step comprising obtaining a Student's t value by performing a Student's t calculation.

24. The method of identifying biomarkers present in human serum which are indicative of pathologies of human lung tissues as recited in claim 23 wherein said second comparing step comprises:

second calculating statistical significances of variances for each biomarker selected during said selecting step between said population of humans with said non-small cell lung cancers and said population of humans without said pathologies of said human lung tissues, said second calculating step comprising obtaining a Student's t value by performing a Student's t calculation.

25. The method of identifying biomarkers present in human serum which are indicative of pathologies of human lung tissues as recited in claim 24 wherein said third comparing step comprises:

third calculating statistical significances of variances for each biomarker selected during said selecting step between said population of humans with said asthma and said population of humans with said non-small cell lung cancers, said third calculating step comprising obtaining a Student's t value by performing a Student's t calculation.

26. The method of identifying biomarkers present in human serum which are indicative of pathologies of human lung tissues as recited in claim 21 wherein said first comparing step comprises:

first calculating statistical significances of variances for each biomarker selected during said selecting step between said population of humans with said asthma and said population of humans without said pathologies of said human lung tissues, said first calculating step comprising obtaining a Student's t value by performing a Student's t calculation.

27. The method of identifying biomarkers present in human serum which are indicative of pathologies of human lung tissues as recited in claim 26 wherein said second comparing step comprises:

second calculating statistical significances of variances for each biomarker selected during said selecting step between said population of humans with said non-small cell lung cancers and said population of humans without said pathologies of said human lung tissues, said second calculating step comprising obtaining a Student's t value by performing a Student's t calculation.

28. The method of identifying biomarkers present in human serum which are indicative of pathologies of human lung tissues as recited in claim 27 wherein said third comparing step comprises:

third calculating statistical significances of variances for each biomarker selected during said selecting step between said population of humans with said asthma and said population of humans with said non-small cell lung cancers, said third calculating step comprising obtaining a Student's t value by performing a Student's t calculation.

29. The method of identifying biomarkers present in human serum which are indicative of pathologies of human lung tissues as recited in claim 22 wherein said first comparing step comprises:

first calculating statistical significances of variances for each biomarker selected during said selecting step between said population of humans with said asthma and said population of humans without said pathologies of said human lung tissues, said first calculating step comprising obtaining a Student's t value by performing a Student's t calculation.

30. The method of identifying biomarkers present in human serum which are indicative of pathologies of human lung tissues as recited in claim 29 wherein said second comparing step comprises:

second calculating statistical significances of variances for each biomarker selected during said selecting step between said population of humans with said non-small cell lung cancers and said population of humans without said pathologies of said human lung tissues, said second calculating step comprising obtaining a Student's t value by performing a Student's t calculation.

31. The method of identifying biomarkers present in human serum which are indicative of pathologies of human lung tissues as recited in claim 30 wherein said third comparing step comprises:

third calculating statistical significances of variances for each biomarker selected during said selecting step between said population of humans with said asthma and said population of humans with said non-small cell lung cancers, said third calculating step comprising obtaining a Student's t value by performing a Student's t calculation.

32. The method of identifying biomarkers present in human serum which are indicative of pathologies of human lung tissues as recited in claim 25 wherein said identifying which of said biomarkers selected during said selecting step are indicative of said pathologies of said human lung tissues comprises selecting biomarkers with said Student's t values smaller than 0.05.

33. The method of identifying biomarkers present in human serum which are indicative of pathologies of human lung tissues as recited in claim 28 wherein said identifying which of said biomarkers selected during said selecting step are indicative of said pathologies of said human lung tissues comprises selecting biomarkers with said Student's t values smaller than 0.05.

34. The method of identifying biomarkers present in human serum which are indicative of pathologies of human lung tissues as recited in claim 31 wherein said identifying which of said biomarkers selected during said selecting step are indicative of said pathologies of said human lung tissues comprises selecting biomarkers with said Student's t values smaller than 0.05.

* * * * *